(12) United States Patent
Xie et al.

(10) Patent No.: US 12,351,582 B2
(45) Date of Patent: *Jul. 8, 2025

(54) AURORA KINASE INHIBITORS AND USES THEREOF

(71) Applicant: WIGEN BIOMEDICINE TECHNOLOGY (SHANGHAI) CO., LTD., Shanghai (CN)

(72) Inventors: Yuli Xie, Shanghai (CN); Houxing Fan, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 853 days.

This patent is subject to a terminal disclaimer.

(21) Appl. No.: 17/200,854

(22) Filed: Mar. 14, 2021

(65) Prior Publication Data

US 2021/0198261 A1 Jul. 1, 2021

Related U.S. Application Data

(63) Continuation of application No. PCT/CN2020/098775, filed on Jun. 29, 2020.

(30) Foreign Application Priority Data

Jul. 16, 2019 (CN) .......................... 201910643061.2

(51) Int. Cl.
*C07D 471/14* (2006.01)
*C07D 401/14* (2006.01)

(52) U.S. Cl.
CPC ......... *C07D 471/14* (2013.01); *C07D 401/14* (2013.01); *C07B 2200/05* (2013.01)

(58) Field of Classification Search
CPC .. C07D 471/14; C07D 401/14; C07D 417/14; C07B 2200/05; A61P 35/02; A61P 35/00; A61K 31/4545
See application file for complete search history.

(56) References Cited

U.S. PATENT DOCUMENTS

2015/0065479 A1 * 3/2015 Hirai .................... A61K 31/415
514/210.18

FOREIGN PATENT DOCUMENTS

| CN | 104159893 | A | | 11/2014 | |
|---|---|---|---|---|---|
| CN | 107108567 | A | * | 8/2017 | ......... A61K 31/4545 |
| JP | 2009520791 | A | | 5/2009 | |
| JP | 2011514309 | A | | 5/2011 | |
| JP | 2016539942 | A | | 12/2016 | |
| WO | 2009104802 | A1 | | 8/2009 | |
| WO | 2013129443 | A1 | | 9/2013 | |
| WO | 2016077161 | A1 | | 5/2016 | |
| WO | 2018117267 | A1 | | 6/2018 | |
| WO | 2021147974 | A1 | | 7/2021 | |

OTHER PUBLICATIONS

Natalya I. Vasilevich et al., "General Ser/Thr Kinases Pharmacophore Approach for Selective Kinase Inhibitors Search as Exemplified by Design of Potent and Selective Aurora A Inhibitors," Chem Biol Drug Des 2016; 88: 54-65 (Jan. 30, 2016).
Natalya I. Vasilevich et al, "Search for Potent and Selective Aurora A Inhibitors Based on General Ser/Thr Kinase Pharmacophore Model," Pharmaceuticals, No. 9, No. 2, pp. 1-14 (Apr. 13, 2016).

* cited by examiner

*Primary Examiner* — Jeffrey H Murray
*Assistant Examiner* — Luisalberto Gonzalez
(74) *Attorney, Agent, or Firm* — SZDC Law PC

(57) ABSTRACT

The invention relates to a type of novel pyridine compound and a preparation method and application thereof. Specifically, the invention relates to a compound of formula (1) and a preparation method thereof, and an application of the compound of formula (1) and pharmaceutically acceptable salts thereof as aurora kinase inhibitors in preparation of anti-tumor drugs.

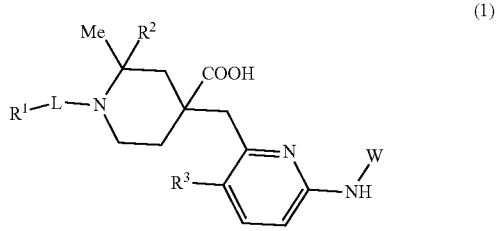

(1)

6 Claims, No Drawings

AURORA KINASE INHIBITORS AND USES THEREOF

This application is a Continuation Application of PCT/CN2020/098775, filed on Jun. 29, 2020, which claims the benefits of Chinese Patent Application No. 201910643061.2, filed on Jul. 16, 2019, which is incorporated herein by reference in its entirety.

FIELD OF THE INVENTION

The invention relates to the fields of pharmaceuticals, medicinal chemistry and pharmacology, and more specifically, relates to a kind of aurora kinase inhibitors, the preparation methods and the uses thereof.

BACKGROUND OF THE INVENTION

Aurora kinase are serine/threonine kinases that play essential roles in centrosome duplication, spindle formation, chromosome segregation and spindle assembly checkpoint during mitosis [Cancer Metastasis Rev., 2003, 22, 451]. There are three structurally and functionally related aurora kinases, Aurora-A, Aurora-B and Aurora-C. Aurora-A localizes next to the centrosome during early mitosis, and associates with spindle microtubules and mitotic poles through metaphase and telophase. It is required for centrosome duplication, maturation and separation, and the formation of bipolar spindles, and orchestrates the entry and exit of mitosis [Nat. Rev. Cancer, 2005, 5, 42]. Aurora-B localizes to the centrosome around the chromatin in early mitosis, and to the mitotic spindle in anaphase. It is a key player in centrosome function, chromosome alignment and separation, spindle checkpoint, and cytokinesis [Mol. Cancer Ther., 2009, 8, 2046-2056]. Roles of Aurora-C in mitosis is poorly defined. It is expressed at a high level in testis and may play a specialized role in male animals [Proc Natl Acad Sci USA, 2002, 99 (24): 15440-15445].

The gene encoding Aurora-A maps to 20q13.2, a region that is frequently amplified in cancers including breast cancer, colon cancer, ovarian cancer and thyroid cancer. Ectopic expression of Aurora A in normal cells resulted in centrosome amplification, aneuploidy, chromosome instability, and telomere elongation, characteristics associated with transformed cells [J. Cell Sci., 2007, 120, 2987]. Overexpression of Aurora-A or its activating partner TPX-2 is believed to contribute to chromosome instability in human cancer. In addition, Aurora-A regulates the function of tumor suppressors and pro-apoptotic proteins such as p53. For example, phosphorylation of p53 at Ser215 and Ser351 by Aurora A promotes its functional inactivation and degradation, respectively.

The gene encoding Aurora-B maps to 17p13.1, a chromosome region that is sometimes deleted or amplified in certain cancer [J. Clin. Pathol., 2007, 60 (2): 218-221]. Elevated expression of Aurora-B mRNA and protein is observed in colon cancer, oral cancer and non-small cell lung cancer. Aurora-B is a subunit of chromosome passenger complex (CPC). Aurora-B regulates mitosis through phosphorylation of INCENP, CENP-A and Survivin. In addition, overexpression of Aurora-B was also shown to enhance ras signaling.

Aurora kinases have become drug-targets for anti-cancer therapeutics due to their oncogenic property. Aurora kinase inhibitors have been developed as novel anti-cancer agents, among which LY-3295668 with a pyridine core is an Aurora A specific inhibitor in phase I development [WO2016077161]. The structure of LY-3295668 is listed below.

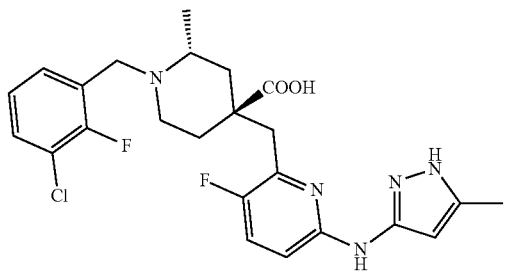

However, LY-3295668 and other Aurora-A inhibitors are invariably associated with weak activity, poor oral bioavailability or moderate in vivo efficacy. Therefore, development of novel Aurora inhibitors with improved in vitro and in vivo activity is warranted.

SUMMARY OF THE INVENTION

The present invention provides a novel kinase inhibitor of general formula (1), an optical isomer, a crystalline form, a pharmaceutically acceptable salt thereof:

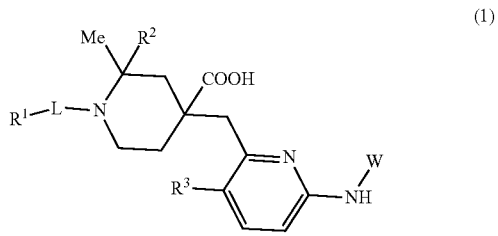

In formula (1):
$R^1$ is aryl, heteroaryl,

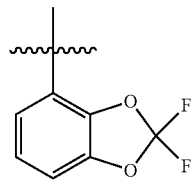 [SMILES: *c1cccc2c1OC(F)(F)O2]

or

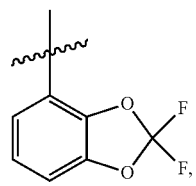 [SMILES: *c1cccc2c1OC(F)(F)O2]

wherein the aryl and the heteroaryl is optionally substituted by 1-3 groups selecting from halogen, C1-C3 alkyl, C1-C3 alkoxyl, halogen substituted C1-C3 alkyl or halogen substituted C1-C3 alkoxyl;

$R^2$ is H or methyl;
$R^3$ is H or F;
W is

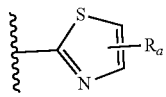

or

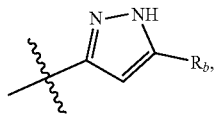

wherein $R_a$ is H, C1-C3 alkyl or C3-C6 cycloalkyl, $R_b$ is H, C1-C3 alkyl or C3-C6 cycloalkyl; and L is $CH_2$, CO, $CD_2$, CH(Me), $C(Me)_2$,

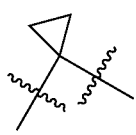 [SMILES: *C1(*)CC1]

or

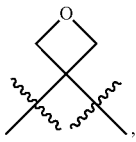 [SMILES: *C1(*)COC1]

when W is

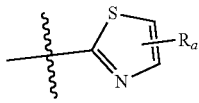

or

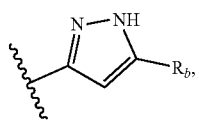

and $R_b$ is H, C2-C3 alkyl or C3-C6 cycloalkyl; or L is CO, $CD_2$, CHMe, $C(Me)_2$,

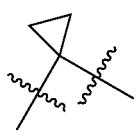 [SMILES: *C1(*)CC1]

or

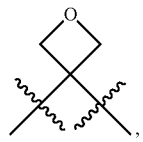 [SMILES: *C1(*)COC1]

when W is

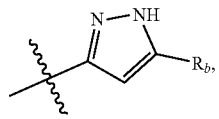

and $R_b$ is methyl.

In another preferred embodiment, in formula (1), $R^1$ is

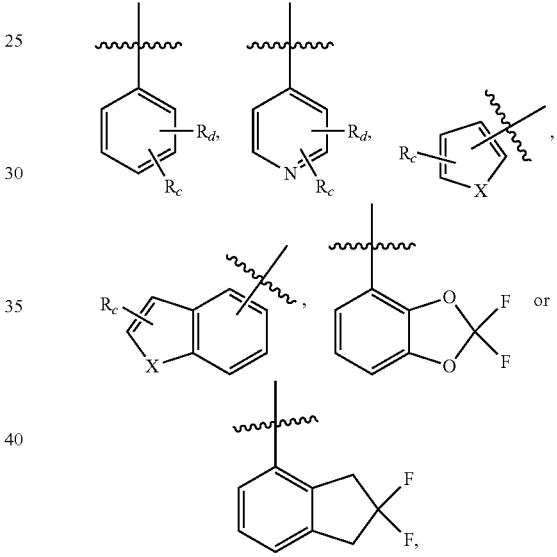

wherein X is NH, O or S, $R_c$ and $R_d$ are independently H, halogen, C1-C3 alkyl, C1-C3 alkoxyl, halogen substituted C1-C3 alkyl or halogen substituted C1-C3 alkoxyl.

In another preferred embodiment, in formula (1), $R^1$ is

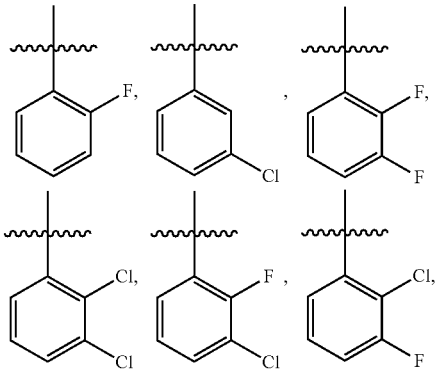

-continued
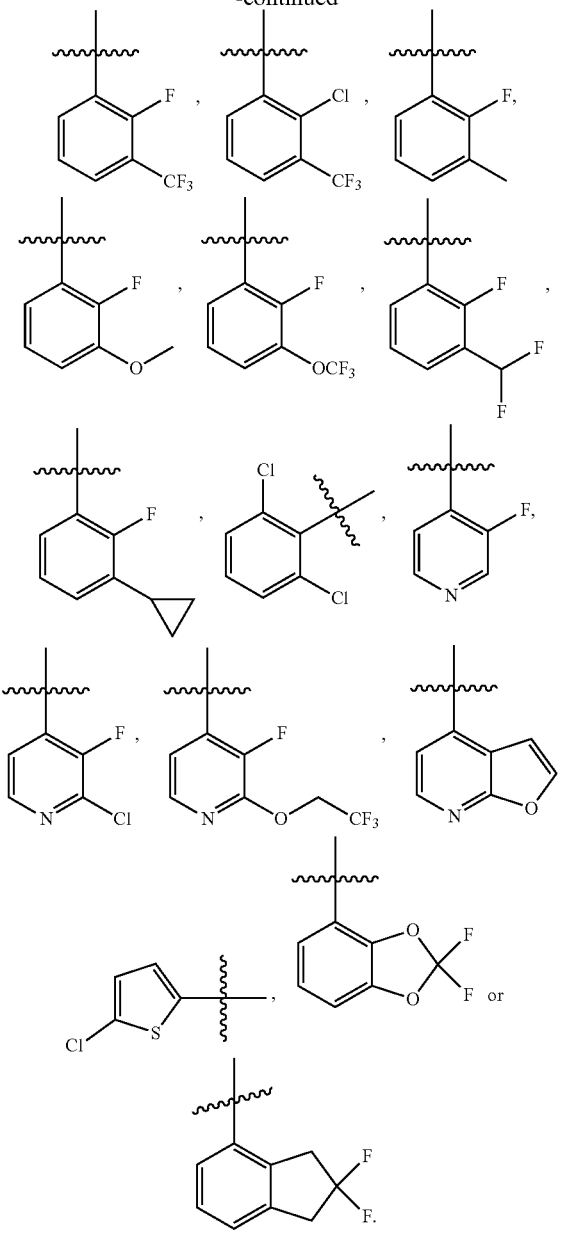
In another preferred embodiment, in formula (1), W is selected from:
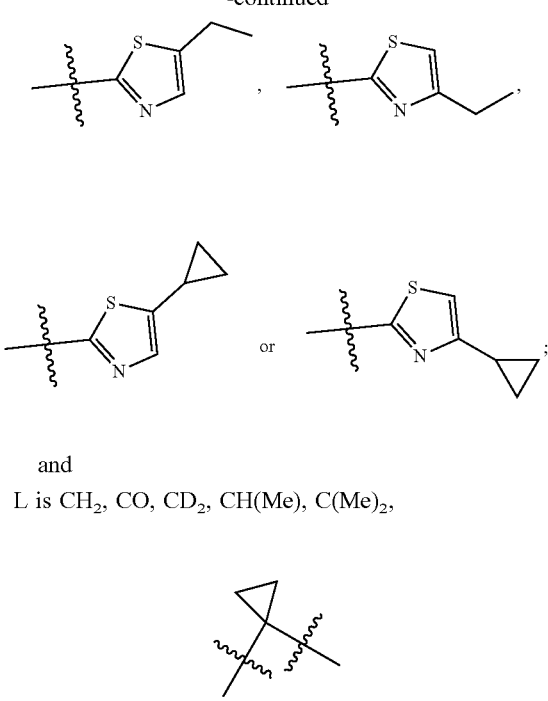
and
L is $CH_2$, CO, $CD_2$, CH(Me), $C(Me)_2$,
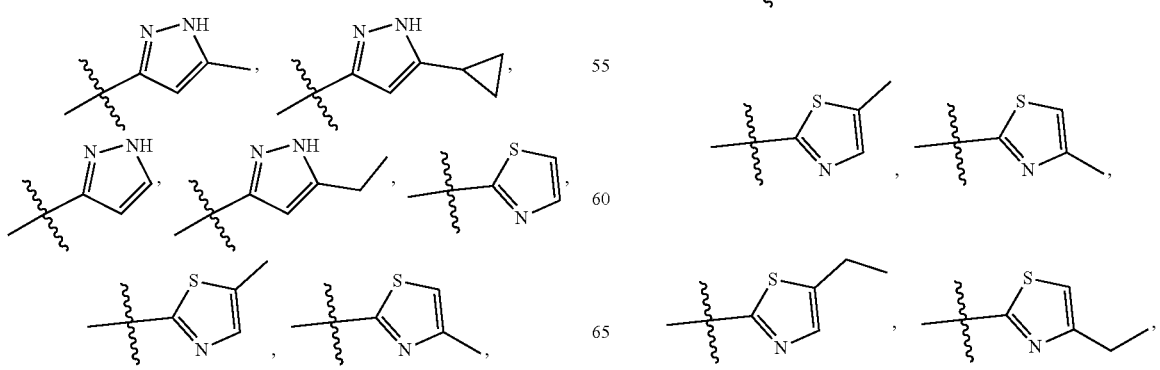
when W is

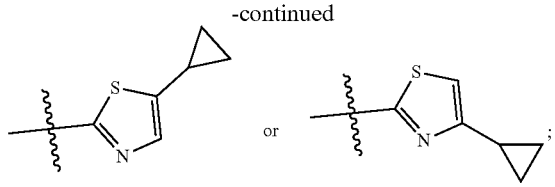

or L is CO, CD₂, CHMe, C(Me)₂,

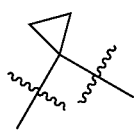 [SMILES: *C1(*)CC1]

or when W is

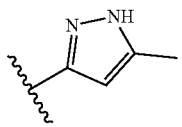

Through synthesizing and carefully studying of a variety of new compounds involving inhibition of aurora kinase, the inventors have found that for the compounds of the general formula (1), when -L- group is changed from CH₂ to an appropriate size group, such as CD₂, and/or when W is

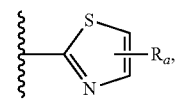

these compounds have extremely strong aurora-A kinase inhibitory activity while aurora-B activity and in vivo antitumor activity are also greatly improved.

In another preferred embodiment, the compound of general formula (1) is selected from the compounds listed in Table 1.

TABLE 1

Compounds of the Invention

| No. | Structure | Name |
|---|---|---|
| 1 | 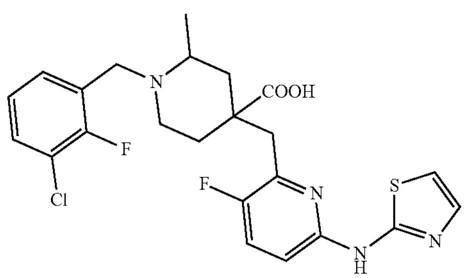 [SMILES: CC1CC(Cc2nc(Nc3nccs3)ccc2F)(C(=O)O)CCN1Cc1cccc(Cl)c1F] | 1-(3-chloro-2-fluorobenzyl)-4-((3-fluoro-6-(thiazol-2-ylamino)pyridin-2-yl)methyl)-2-methylpiperidine-4-carboxylic acid |
| 2 | 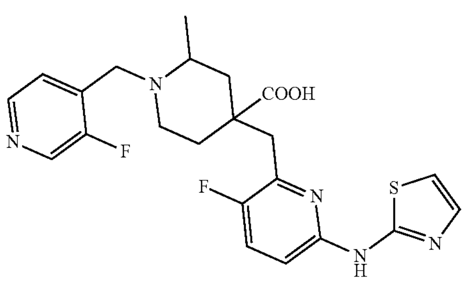 [SMILES: CC1CC(Cc2nc(Nc3nccs3)ccc2F)(C(=O)O)CCN1Cc1ccncc1F] | 4-((3-fluoro-6-(thiazol-2-ylamino)pyridin-2-yl)methyl)-1-((3-fluoropyridin-4-yl)methyl)-2-methylpiperidine-4-carboxylic acid |
| 3 | 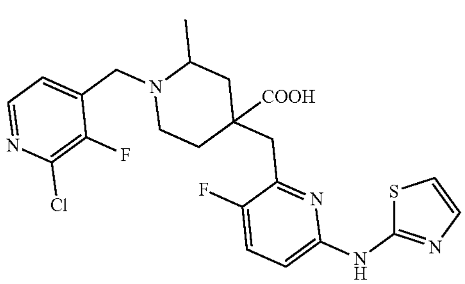 [SMILES: CC1CC(Cc2nc(Nc3nccs3)ccc2F)(C(=O)O)CCN1Cc1ccnc(Cl)c1F] | 1-((2-chloro-3-fluoropyridin-4-yl)methyl)-4-((3-fluoro-6-(thiazol-2-ylamino)pyridin-2-yl)methyl)-2-methylpiperidine-4-carboxylic acid |

TABLE 1-continued

Compounds of the Invention

| No. | Structure | Name |
|---|---|---|
| 4 | 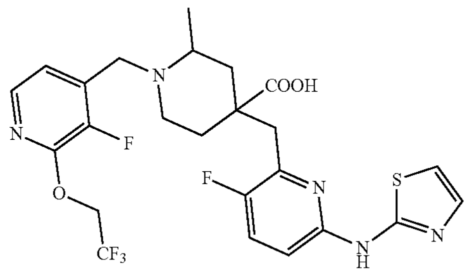 [SMILES: CC1CC(Cc2nc(Nc3nccs3)ccc2F)(C(=O)O)CCN1Cc1ccnc(OCC(F)(F)F)c1F] | 1-((3-fluoro-2-(2,2,2-trifluoroethoxy)pyridin-4-yl)methyl)-4-((3-fluoro-6-(thiazol-2-ylamino)pyridin-2-yl)methyl)-2-methylpiperidine-4-carboxylic acid |
| 5 | 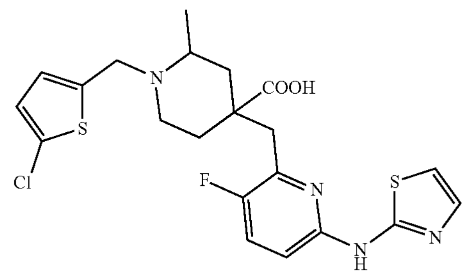 [SMILES: CC1CC(Cc2nc(Nc3nccs3)ccc2F)(C(=O)O)CCN1Cc1ccc(Cl)s1] | 1-((5-chlorothiophen-2-yl)methyl)-4-((3-fluoro-6-(thiazol-2-ylamino)pyridin-2-yl)methyl)-2-methylpiperidine-4-carboxylic acid |
| 6 | 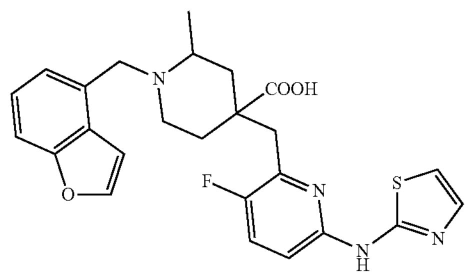 [SMILES: CC1CC(Cc2nc(Nc3nccs3)ccc2F)(C(=O)O)CCN1Cc1cccc2occc12] | 1-(benzofuran-4-ylmethyl)-4-((3-fluoro-6-(thiazol-2-ylamino)pyridin-2-yl)methyl)-2-methylpiperidine-4-carboxylic acid |
| 7 | 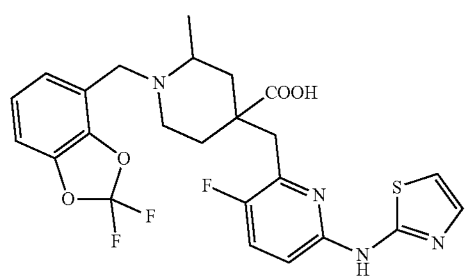 [SMILES: CC1CC(Cc2nc(Nc3nccs3)ccc2F)(C(=O)O)CCN1Cc1cccc2c1OC(F)(F)O2] | 1-((2,2-difluorobenzo[d][1,3]dioxol-4-yl)methyl)-4-((3-fluoro-6-(thiazol-2-ylamino)pyridin-2-yl)methyl)-2-methylpiperidine-4-carboxylic acid |
| 8 | 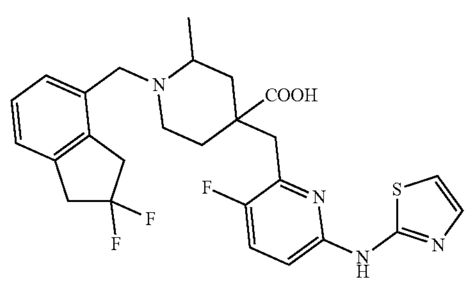 [SMILES: CC1CC(Cc2nc(Nc3nccs3)ccc2F)(C(=O)O)CCN1Cc1cccc2c1CC(F)(F)C2] | 1-((2,2-difluoro-2,3-dihydro-1H-inden-4-yl)methyl)-4-((3-fluoro-6-(thiazol-2-ylamino)pyridin-2-yl)methyl)-2-methylpiperidine-4-carboxylic acid |

TABLE 1-continued

Compounds of the Invention

| No. | Structure | Name |
|---|---|---|
| 9 | 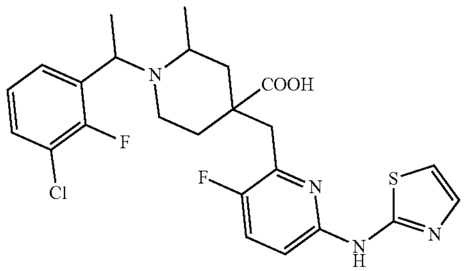 [SMILES: CC1CC(Cc2nc(Nc3nccs3)ccc2F)(C(=O)O)CCN1C(C)c1cccc(Cl)c1F] | 1-(1-(3-chloro-2-fluorophenyl)ethyl)-4-((3-fluoro-6-(thiazol-2-ylamino)pyridin-2-yl)methyl)-2-methylpiperidine-4-carboxylic acid |
| 10 | 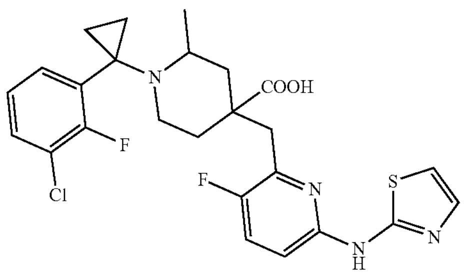 [SMILES: CC1CC(Cc2nc(Nc3nccs3)ccc2F)(C(=O)O)CCN1C1(c2cccc(Cl)c2F)CC1] | 1-(1-(3-chloro-2-fluorophenyl)cyclopropyl)-4-((3-fluoro-6-(thiazol-2-ylamino)pyridin-2-yl)methyl)-2-methylpiperidine-4-carboxylic acid |
| 11 | 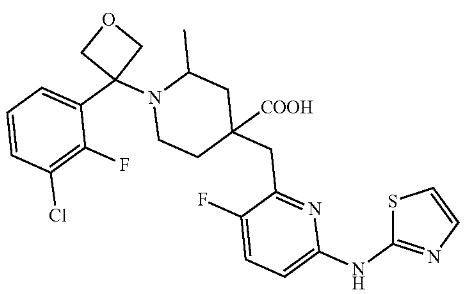 [SMILES: CC1CC(Cc2nc(Nc3nccs3)ccc2F)(C(=O)O)CCN1C1(c2cccc(Cl)c2F)COC1] | 1-(3-(3-chloro-2-fluorophenyl)oxetan-3-yl)-4-((3-fluoro-6-(thiazol-2-ylamino)pyridin-2-yl)methyl)-2-methylpiperidine-4-carboxylic acid |
| 12 | 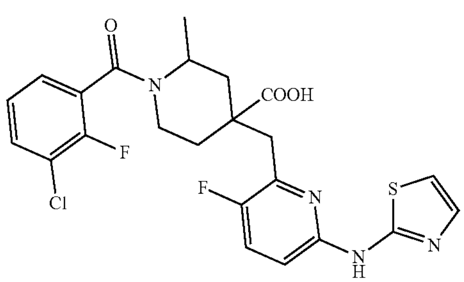 [SMILES: CC1CC(Cc2nc(Nc3nccs3)ccc2F)(C(=O)O)CCN1C(=O)c1cccc(Cl)c1F] | 1-(3-chloro-2-fluorobenzoyl)-4-((3-fluoro-6-(thiazol-2-ylamino)pyridin-2-yl)methyl)-2-methylpiperidine-4-carboxylic acid |
| 13 | 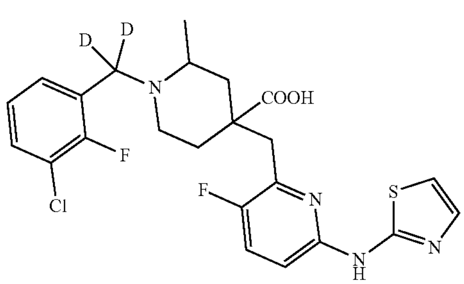 [SMILES: [2H]C([2H])(c1cccc(Cl)c1F)N1CCC(Cc2nc(Nc3nccs3)ccc2F)(C(=O)O)CC1C] | 1-((3-chloro-2-fluorophenyl)methyl-d2)-4-((3-fluoro-6-(thiazol-2-ylamino)pyridin-2-yl)methyl)-2-methylpiperidine-4-carboxylic acid |

TABLE 1-continued

Compounds of the Invention

| No. | Structure | Name |
|---|---|---|
| 14 | 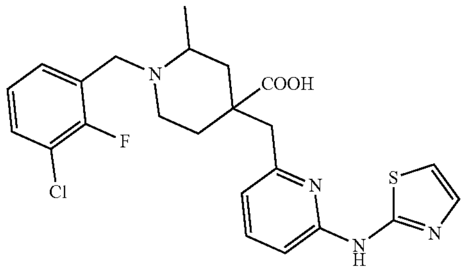 [SMILES: CC1CC(Cc2cccc(Nc3nccs3)n2)(C(=O)O)CCN1Cc1cccc(Cl)c1F] | 1-(3-chloro-2-fluorobenzyl)-2-methyl-4-((6-(thiazol-2-ylamino)pyridin-2-yl)methyl)piperidine-4-carboxylic acid |
| 15 | 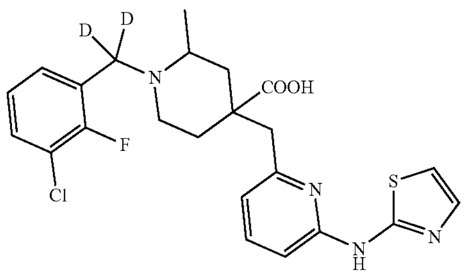 [SMILES: [2H]C([2H])(c1cccc(Cl)c1F)N1CCC(Cc2cccc(Nc3nccs3)n2)(C(=O)O)CC1C] | 1-((3-chloro-2-fluorophenyl)methyl-$d_2$)-2-methyl-4-((6-(thiazol-2-ylamino)pyridin-2-yl)methyl)piperidine-4-carboxylic acid |
| 16 | 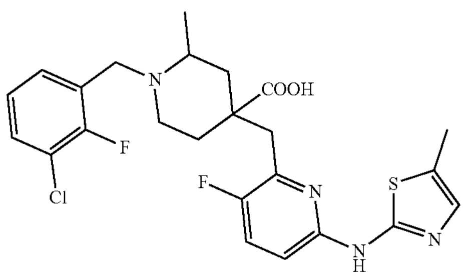 [SMILES: Cc1cnc(Nc2ccc(F)c(CC3(C(=O)O)CCN(Cc4cccc(Cl)c4F)C(C)C3)n2)s1] | 1-(3-chloro-2-fluorobenzyl)-4-((3-fluoro-6-((5-methylthiazol-2-yl)amino)pyridin-2-yl)methyl)-2-methylpiperidine-4-carboxylic acid |
| 17 | 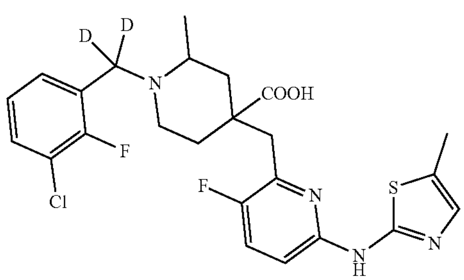 [SMILES: [2H]C([2H])(c1cccc(Cl)c1F)N1CCC(Cc2nc(Nc3ncc(C)s3)ccc2F)(C(=O)O)CC1C] | 1-((3-chloro-2-fluorophenyl)methyl-$d_2$)-4-((3-fluoro-6-((5-methylthiazol-2-yl)amino)pyridin-2-yl)methyl)-2-methylpiperidine-4-carboxylic acid |
| 18 | 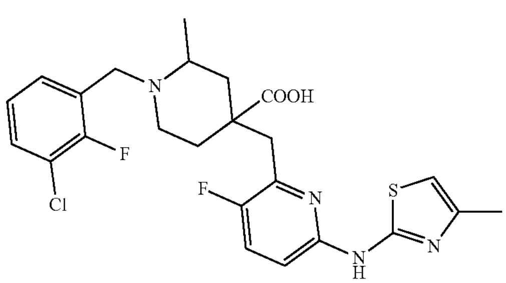 [SMILES: Cc1csc(Nc2ccc(F)c(CC3(C(=O)O)CCN(Cc4cccc(Cl)c4F)C(C)C3)n2)n1] | 1-(3-chloro-2-fluorobenzyl)-4-((3-fluoro-6-((4-methylthiazol-2-yl)amino)pyridin-2-yl)methyl)-2-methylpiperidine-4-carboxylic acid |

TABLE 1-continued

Compounds of the Invention

| No. | Structure | Name |
|---|---|---|
| 19 | 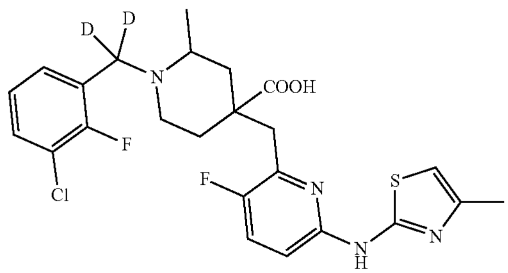 [SMILES: [2H]C([2H])(c1cccc(Cl)c1F)N1CCC(Cc2nc(Nc3nc(C)cs3)ccc2F)(C(=O)O)CC1C] | 1-((3-chloro-2-fluorophenyl)methyl-d$_2$)-4-((3-fluoro-6-((4-methylthiazol-2-yl)amino)pyridin-2-yl)methyl)-2-methylpiperidine-4-carboxylic acid |
| 20 | 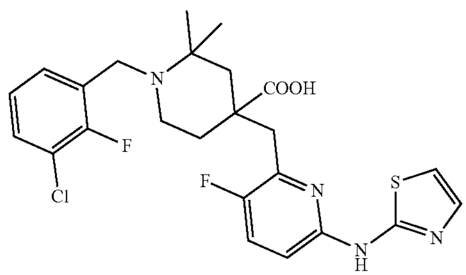 [SMILES: CC1(C)CC(Cc2nc(Nc3nccs3)ccc2F)(C(=O)O)CCN1Cc1cccc(Cl)c1F] | 1-(3-chloro-2-fluorobenzyl)-4-((3-fluoro-6-(thiazol-2-ylamino)pyridin-2-yl)methyl)-2,2-dimethylpiperidine-4-carboxylic acid |
| 21 | 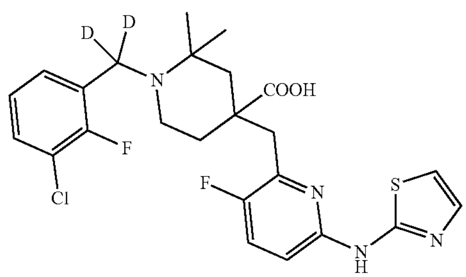 [SMILES: [2H]C([2H])(c1cccc(Cl)c1F)N1CCC(Cc2nc(Nc3nccs3)ccc2F)(C(=O)O)CC1(C)C] | 1-((3-chloro-2-fluorophenyl)methyl-d$_2$)-4-((3-fluoro-6-(thiazol-2-ylamino)pyridin-2-yl)methyl)-2,2-dimethylpiperidine-4-carboxylic acid |
| 22 | 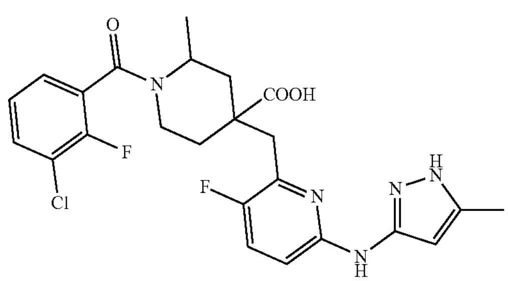 [SMILES: Cc1cc(Nc2ccc(F)c(CC3(C(=O)O)CCN(C(=O)c4cccc(Cl)c4F)C(C)C3)n2)n[nH]1] | 1-(3-chloro-2-fluorobenzoyl)-4-((3-fluoro-6-((5-methyl-1H-pyrazol-3-yl)amino)pyridin-2-yl)methyl)-2-methylpiperidine-4-carboxylic acid |
| 23 | 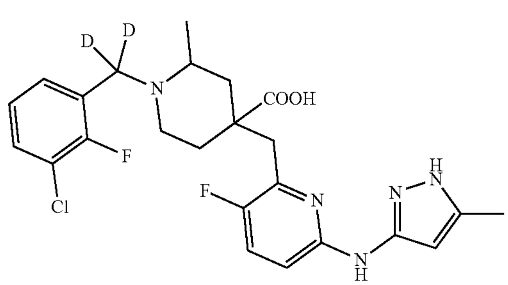 [SMILES: [2H]C([2H])(c1cccc(Cl)c1F)N1CCC(Cc2nc(Nc3cc(C)[nH]n3)ccc2F)(C(=O)O)CC1C] | 1-((3-chloro-2-fluorophenyl)methyl-d$_2$)-4-((3-fluoro-6-((5-methyl-1H-pyrazol-3-yl)amino)pyridin-2-yl)methyl)-2-methylpiperidine-4-carboxylic acid |

TABLE 1-continued

Compounds of the Invention

| No. | Structure | Name |
|---|---|---|
| 24 | 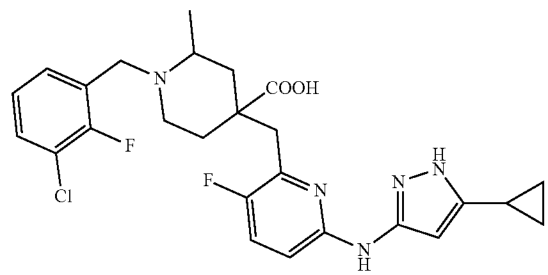 [SMILES: CC1CC(Cc2nc(Nc3cc(C4CC4)[nH]n3)ccc2F)(C(=O)O)CCN1Cc1cccc(Cl)c1F] | 1-(3-chloro-2-fluorobenzyl)-4-((6-((5-cyclopropyl-1H-pyrazol-3-yl)amino)-3-fluoropyridin-2-yl)methyl)-2-methylpiperidine-4-carboxylic acid |

In another embodiment, the invention provides a combination pharmaceutical composition, which contains a pharmacologically acceptable excipient or carrier, and the compound of formula (1) of the present invention, an optical isomer, or a pharmaceutically acceptable salt thereof, as an active ingredient.

In another embodiment, the invention provides the use of the compound, an optical isomer, or pharmaceutically acceptable salt thereof, in the manufacture of drugs for treating diseases related to aurora kinase, especially the application in anti-tumor drugs.

DETAILED DESCRIPTION OF THE ILLUSTRATED EMBODIMENTS

The preparation methods of the compounds of the general formula (1) are described specifically in following part, but these specific methods do not constitute any limitations of the present invention.

The compounds of formula (1) described above may be synthesized using standard synthesis techniques, well-known techniques or combination of the methods herein. In addition, the solvents, temperatures and other reaction conditions mentioned herein may vary. Starting materials for the synthesis of the compound of formula (1) may be synthesized or obtained from commercial sources such as, but not limited to, Aldrich Chemical Co. (Milwaukee, Wis.) or Sigma Chemical Co. (St. Louis, Mo.). The compounds described herein and other related compounds having different substituents may be synthesized using well-known techniques and starting materials, including those found in March, ADVANCED ORGANIC CHEMISTRY 4th Ed. (Wiley 1992); Carey and Sundberg, ADVANCED ORGANIC CHEMISTRY 4th Ed., Vols. A and B (Plenum 2000, 2001), Green and Wuts, Protective Groups in Organic Synthesis 3$^{rd}$ Ed., (Wiley 1999). The general methods for the preparation of the compounds can be varied by using suitable reagents and conditions for introducing different groups in the molecular formulas provided herein.

In one aspect, the compounds described herein are obtained according to the well-known methods. However, the conditions of the process such as reactants, solvents, bases, amounts of compound used, reaction temperatures, time required for the reactions, and the like are not limited to the following explanations. The compounds of the invention may also be conveniently prepared, optionally in combination with various synthetic methods described in this specification or well-known methods, such combinations being readily carried out by those skilled in the art. On the other aspect, the invention also provides the preparation methods of the compounds shown in the general formula (1), which are prepared by the following method A or method B:

Method A contains the following steps: First, starting materials A and B are conducted to coupling reaction to afford compound C under the basic condition with palladium catalyst and ligand, Second, Compound C is de-protected Boc group under acidic condition to get compound D, then compound D react with R$^1$-L-X to get compound E, and finally compound E is hydrolyzed under acidic or basic condition to give the compound of formula (1a).

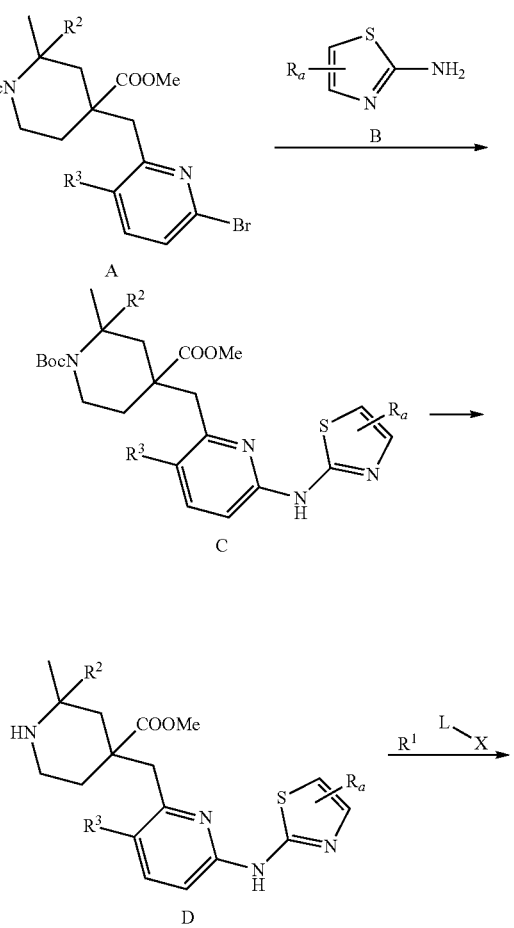

-continued

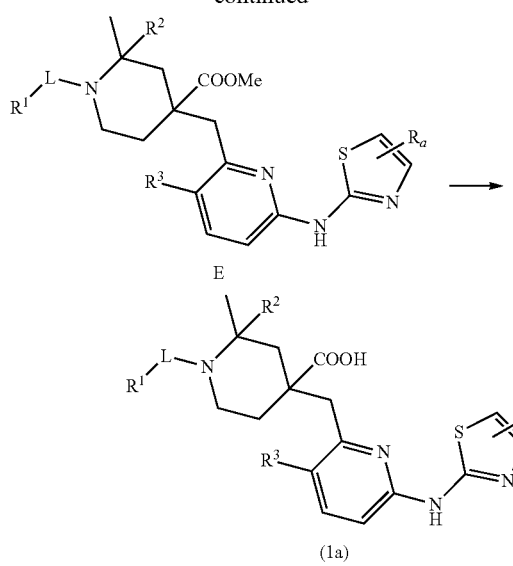

(1a)

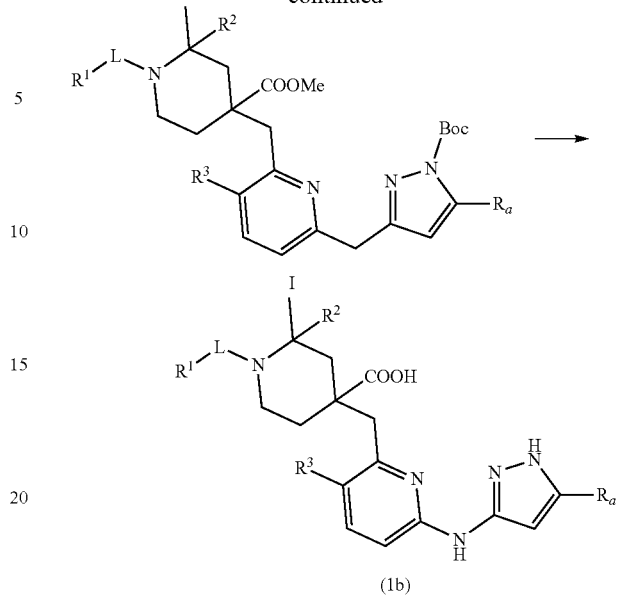

(1b)

In the above reaction, $R^1, R^2, R^3, R_a$ and L have the same definitions as defined above, X is selected from Br, Cl, OTf or OH.

Method B contains the following steps: First, starting materials F react with B to afford compound G, Second, compound G and H are conducted to coupling reaction to afford compound I under the basic condition with palladium catalyst and ligand, and finally compound I is hydrolyzed under strong acidic condition to give the compound of formula (1b).

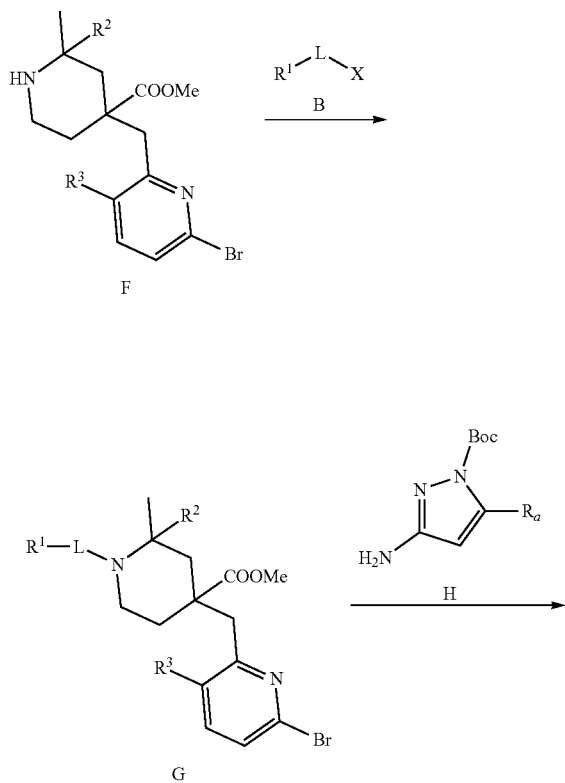

In the above reaction, $R^1, R^2, R^3, R_a$ and L have the same definitions as defined above, X is selected from Br, Cl, OTf or OH.

FURTHER FORMS OF THE COMPOUNDS

The term "pharmaceutically acceptable salt" refers to a form of a compound that does not cause significant irritation to the administered subject and does not eliminate the biological activities and properties of the compound. The salt of the compound of the present invention refers to a salt conventionally used in the field of organic chemistry, and can be, for example, a salt of a base addition salt wherein the compound having a carboxyl group, or a salt of an acid addition salt wherein the compound having an amine group or a basic heterocyclic group.

Example of that base addition salt includes alkali metal salt such as sodium salt and potassium salt, alkaline earth metal salt such as calcium and magnesium salts; ammonium salt such as trimethylamine salt, triethylamine salt, dicyclohexylamine salt, ethanolamine salt, diethanolamine salt, triethanolamine salt, procaine salt, N,N'-dibenzylethylenediamine salt, and the like.

Example of that acid addition salt includes inorganic acid salt such as hydrochloride, sulfate, nitric acid, and phosphate; organic acid salt such as acetate, formate, maleate, fumarate, citrate, oxalate, ascorbate and other organic acid salt; sulfonate such as methanesulfonate, benzenesulfonate, p-toluenesulfonate, and that like.

It should be understood that pharmaceutically acceptable salts include solvent addition forms or crystalline forms, especially solvates or polymorphs. Solvates contain stoichiometric or non-stoichiometric solvents and are selectively formed during crystallization with pharmaceutically acceptable solvents such as water and ethanol. Hydrates are formed when the solvent is water, or alcoholates are formed when the solvent is ethanol. The solvates of the compound of formula (1) can be conveniently prepared or formed according to the method described herein. For example, the hydrate of the compound of formula (1) is conveniently prepared by recrystallization from a mixed solvent of water/organic solvent, and the organic solvent used includes but is not limited to dioxane, tetrahydrofuran, ethanol or methanol. In addition, the compounds mentioned here can exist in non-solvated or solvated forms. In summary, for the purposes of the compounds and methods provided herein, the solvated forms are considered to be equivalent to the non-solvated forms.

In other specific embodiments, the compounds of formula (1) are prepared in different forms, including but not limited to amorphous, pulverized and nano-particle size forms. In addition, the compounds of formula (1) include crystalline forms and polymorphic forms. Polymorphic forms include different lattice arrangements of the same element composition of the compounds. Polymorphs usually have different X-ray diffraction patterns, infrared spectra, melting points, density, hardness, crystalline forms, optical and electrical properties, stability and solubility. Different factors, such as recrystallization solvent, crystallization rate and storage temperature, may cause specific crystalline formed dominantly.

On the other aspect, the compounds of formula (1) have one or more stereocenters, and thus appear in the forms of racemate, racemic mixture, single enantiomer, diastereomer compound and single diastereomer. The asymmetric centers that can exist depend on the properties of various substituents on the molecule. Each such asymmetric center will independently produce two optical isomers, and all possible optical isomers and diastereomer mixtures and pure or partially pure compounds are included in the scope of the present invention. The present invention is meant to include all such isomeric forms of these compounds.

THERAPEUTIC USE

Compounds or compositions described herein can generally be used to inhibit aurora kinase, and thus can be used to treat one or more diseases related to aurora kinase. Therefore, in certain embodiments, the present invention provides a method for treating an aurora kinase-mediated disease, comprising the step of administering a compound of the present invention, or a pharmaceutically acceptable composition thereof, to a patient in need thereof.

Cancers that can be treated with the compounds of the present invention include, but are not limited to, hematological malignancies (leukemia, lymphoma, myeloma including multiple myeloma, myelodysplastic syndrome or myelodysplastic syndrome) and solid tumors (cancers such as prostate, breast, lung, colon, pancreas, kidney, ovary, soft tissue cancer and osteosarcoma or stromal tumors).

ROUTE OF ADMINISTRATION

The compound of the present invention and its pharmaceutically acceptable salts can be made into various preparations, which contain the compound of the present invention or its pharmaceutically acceptable salts and pharmaceutically acceptable excipients or carriers in a safe and effective amount range. Among them, "safe and effective amount" means that the amount of the compound is capable of obviously improving the condition without causing serious side effects. The safe and effective dose of the compound is determined according to the age, illness, course of treatment and other specific conditions of the subject.

"Pharmaceutically acceptable excipient or carrier" refers to one or more compatible solid or liquid fillers or gel substances, which are suitable for human use and must have sufficient purity and low toxicity. "Compatibility" here means that each component in the composition can be mixed with the compounds of the present invention and between them, without significantly reducing the efficacy of the compound. Examples of pharmaceutically acceptable excipients or carriers include cellulose and its derivatives (such as sodium carboxymethyl cellulose, sodium ethyl cellulose, cellulose acetate, etc.), gelatin, talc, solid lubricants (such as stearic acid and magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween), wetting agent (such as sodium dodecyl sulfate), coloring agent, flavoring agent, stabilizer, antioxidant, preservative, pyrogen-free water, etc.

The compounds of the present invention can be administered orally, rectally, parenterally (intravenously, intramuscularly or subcutaneously) or topically.

Solid dosage forms for oral administration include capsules, tablets, pills, powders and granules. In these solid dosage forms, that active compound is mixed with at least one conventional inert excipient (or carry), such as sodium citrate or dicalcium phosphate, or with: (a) a filler or compatibilizer, such as starch, lactose, sucrose, glucose, mannitol, and silicic acid; (b) binders such as hydroxymethyl cellulose, alginates, gelatin, polyvinyl pyrrolidone, sucrose and acacia; (c) humectant, such as glycerol; (d) disintegrant such as agar, calcium carbonate, potato or tapioca starch, alginic acid, certain complex silicates, and sodium carbonate; (e) slow solvents, such as paraffin; (f) an absorption accelerator, such as a quaternary amine compound; (g) wetting agents, such as cetyl alcohol and glyceryl monostearate; (h) adsorbent, such as kaolin; And (i) a lubricant such as talc, calcium stearate, magnesium stearate, solid polyethylene glycol, sodium lauryl sulfate, or mixtures thereof. In capsule, tablets and pill, the dosage form may also contain a buffer.

Solid dosage forms such as tablets, sugar pills, capsules, pills and granules may be prepared using coatings and shell materials such as casings and other materials well-known in the art. They may comprise an opacifying agent and the release of the active compound or compound in such a composition may be released in a delayed manner in a portion of the digestive tract. Examples of embedding components that may be used are polymeric substances and waxes. If desired, the active compound may also form microcapsules with one or more of the above excipients.

Liquid dosage forms for oral administration include pharmaceutically acceptable emulsions, solutions, suspensions, syrups or tinctures. In addition to the active compound, the liquid dosage form may comprise inert diluents conventionally used in the art, such as water or other solvents, solubilizers and emulsifiers, for example ethanol, isopropanol, ethyl carbonate, ethyl acetate, propylene glycol, 1,3-butanediol, dimethylformamide and oils, particularly cottonseed oil, peanut oil, corn germ oil, olive oil, castor oil, sesame oil or mixtures of these and the like.

In addition to these inert diluents, the composition may also contain adjuvants such as wetting agents, emulsifiers and suspending agents, sweeteners, flavoring agents and flavorants.

In addition to the active compounds, the suspension may comprise suspending agents such as ethoxylated isostearyl alcohol, polyoxyethylene sorbitol and sorbitan esters, microcrystalline cellulose, aluminum methoxide, agar or mixtures of these and the like.

The composition for parenteral injection may comprise a physiologically acceptable sterile aqueous or non-aqueous solution, dispersion, suspension or emulsion, and a sterile powder for reconstitution into a sterile injectable solution or dispersion. Suitable aqueous and non-aqueous carriers, diluents, solvents or excipients include water, ethanol, polyols and suitable mixtures thereof.

Dosage forms of the compounds of the invention for topical administration include ointments, powders, patches, sprays and inhalants. The active ingredient is mixed under sterile conditions with a physiologically acceptable carrier and any preservatives, buffers, or propellants as may be required.

The compound of the invention may be administered alone or in combination with other pharmaceutically acceptable compounds.

When a pharmaceutical composition is used, a safe and effective amount of a compound of the invention is applied to a mammal (e.g., a human) in need of treatment, wherein the dose at the time of administration is a pharmaceutically acceptable effective dose, and for a human of 60 kg body weight, the daily dose is generally 1 to 1000 mg, preferably 10 to 500 mg. Of course, specific dose should also take into account factors such as route of administration, patient health, etc., which are within the skill of a skilled physician.

The above features mentioned in the present invention, or the features mentioned in the embodiments, may be combined at random. All of the features disclosed in this specification may be used in any composition form and the various features disclosed in the specification may be replaced with any alternative feature that provides the same, equivalent, or similar purpose. Thus, unless otherwise specified, the disclosed features are merely generic examples of equivalent or similar features.

Various specific aspects, features and advantages of the above compounds, methods, and pharmaceutical compositions will be set forth in detail as following. It is to be understood that the following detailed description and examples describe specific embodiments for reference only. Various changes or modifications may occur to those skilled in the art after reading the description of the invention, and such equivalents fall within the scope of the application.

In all examples, $^1$H-NMR was recorded with a Varian Mercury 400 NMR spectrometer and that chemical shift was expressed as δ (ppm); Silica gel for separation is 200-300 mesh without specific statement, and the ratio of eluents is volume ratio.

Abbreviations of the invention are as following: ACN represents acetonitrile; Ar represents argon; $CBr_4$ represents carbon tetrabromide; $CDCl_3$ represents deuterated chloroform; $CD_3OD$ represents deuterated methanol; DCM represents dichloromethane; DIPEA represents diisopropylethylamine; Diox represents 1,4-dioxane; DMF represents dimethylformamide; DMSO represents dimethyl sulfoxide; EA represents ethyl acetate; EDCI represents 1-(3-Dimethylaminopropyl)-3-ethylcarbodiimide hydrochloride; h represents hour; HOBt represents 1-hydroxybenzotriazole; $K_2CO_3$ represents potassium carbonate; KI represents potassium iodide; $K_3PO_4$ represents potassium phosphate; LC-MS represents Liquid-mass spectrum; $LiAlD_4$ represents lithium aluminum deuteride; LiOH represents lithium hydroxide; mL represents millilitre; MeOH represents methanol; mins represent minutes; MS represents mass spectrum; NMR represents nuclear magnetic resonance; $Pd_2(dba)_3$ represents tris(dibenzylideneacetone)dipalladium; PE represents petroleum ether; $PPh_3$ represents triphenylphosphine; $Tf_2O$ represents trifluoromethanesulfonic anhydride; Xantphos represents 9,9-dimethyl-4,5-bis(diphenylphosphino)xanthene.

DETAILED DESCRIPTION OF THE INVENTION

Example 1 Synthesis of 1-(3-chloro-2-fluorobenzyl)-4-((3-fluoro-6-(thiazol-2-ylamino)pyridin-2-yl)methyl)-2-methylpiperidine-4-carboxylic acid (compound 1)

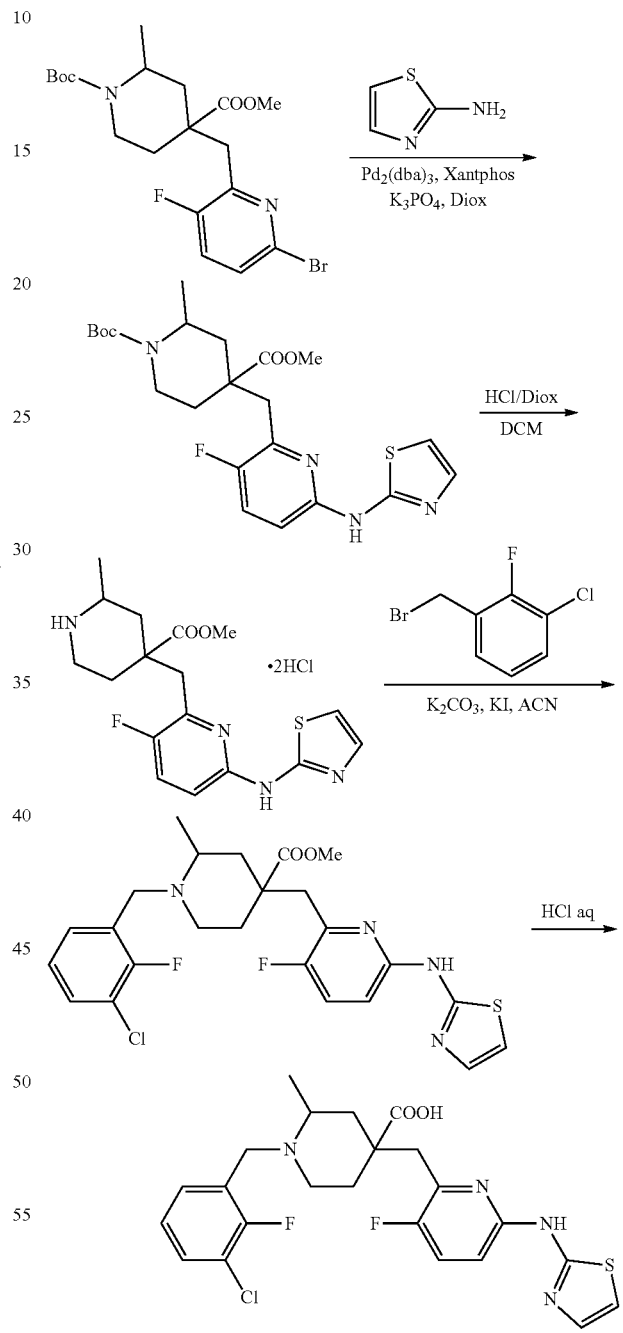

1-(tert-Butyl) 4-methyl 4-((3-fluoro-6-(thiazol-2-ylamino)pyridin-2-yl)methyl)-2-methylpiperidine-1,4-dicarboxylate 1-(tert-Butyl) 4-methyl 4-((6-bromo-3-fluoropyridin-2-yl)methyl)-2-methylpiperidine-1,4-dicarboxylate (5 g, 11.23 mmol, it was synthesized by referring to the method in patent WO2016077161), thiazol-2-amine (956 mg, 9.55 mmol), anhydrous potassium phosphate (6 g, 28.08 mmol), Xantphos (650 mg, 1.123 mmol) and dioxane (100 mL) was added to a 250 mL flask, Pd$_2$(dba)$_3$ (514 mg, 0.562 mmol) was added after the replacement the air by Ar, heated to the refluxing temperature and further reacted for 5 h under the protection of Ar. After the completion of the reaction determined by LC-MS, it was concentrated under reduced pressure, and further purified by column chromatography (DCM/McOH=50/0 to 50/1) to offer the desired product as a yellow solid (4.0 g, yield 89%), ESI-MS m/z: 465.2 [M+H]$^+$.

Methyl 4-((3-fluoro-6-(thiazol-2-ylamino)pyridin-2-yl)methyl)-2-methylpiperidine-4-carboxylate 1-(tert-butyl) 4-methyl 4-((3-fluoro-6-(thiazol-2-ylamino)pyridin-2-yl)methyl)-2-methylpiperidine-1,4-dicarboxylate (4 g, 8.61 mmol) was added to a 100 mL flask, DCM (20 mL) and HCl/Dioxane (22 mL, 4 M, 88 mmol) was added too, followed by stirring at room temperature for 20 h. After the completion of the reaction determined by LC-MS, concentrated, EA (30 mL) was add to the residual and further stirring 30 min, filtered and dried to obtain the target compound as a yellow solid (4.1 g, yield 100%), ESI-MS m/z: 365.2 [M+H]$^+$.

Methyl 1-(3-chloro-2-fluorobenzyl)-4-((3-fluoro-6-(thiazol-2-ylamino)pyridin-2-yl)methyl)-2-methylpiperidine-4-carboxylate Methyl 4-((3-fluoro-6-(thiazol-2-ylamino)pyridin-2-yl)methyl)-2-methylpiperidine-4-carboxylate (800 mg, 1.83 mmol), 1-(bromomethyl)-3-chloro-2-fluorobenzene (500 mg, 2.19 mmol), K$_2$CO$_3$ (1.264 g, 9.15 mmol), KI (20 mg) and ACN (20 mL) was added to a 100 mL flask, then the mixture reacted at room temperature for 2 h. After the completion of the reaction determined by LC-MS, water (100 mL) was added to precipitate the solid, followed by filtration. The filter cake was washed twice with water (20 mL*2) and then slurried with PE (50 mL) After filtration, the filter cake was washed twice with PE (20 mL*2) and dried to obtain the crude product methyl 1-(3-chloro-2-fluorobenzyl)-4-((3-fluoro-6-(thiazol-2-ylamino)pyridin-2-yl)methyl)-2-methylpiperidine-4-carboxylate (935 mg, yield 100%), which was conducted to the next step without further purification. ESI-MS m/z: 510.2 [M+H]$^+$.

1-(3-Chloro-2-fluorobenzyl)-4-((3-fluoro-6-(thiazol-2-ylamino)pyridin-2-yl)methyl)-2-methylpiperidine-4-carboxylic acid Methyl 1-(3-chloro-2-fluorobenzyl)-4-((3-fluoro-6-(thiazol-2-ylamino)pyridin-2-yl)methyl)-2-methylpiperidine-4-carboxylate (935 mg, 1.83 mmol) was added to a 100 mL flask, then water (15 mL) and con. HCl (15 mL) was added, heated to the refluxing temperature and further reacted for 5 h. After the completion of the reaction determined by LC-MS, it was concentrated and the residual was slurried with ACN (30 mL) at room temperature. After filtration, the filter cake was washed with ACN (5 mL*2), and dried to obtain the desired yellow powder (818 mg, yield 90%).

$^1$H NMR (400 MHz, DMSO-d$_6$) δ: 11.68 (s, 1H), 10.59 (s, 1H), 7.76 (t, J=7.2 Hz, 1H), 7.73-7.68 (m, 1H), 7.61 (t, J=9.2 Hz, 1H), 7.43 (d, J=3.7 Hz, 1H), 7.34 (t, J=7.9 Hz, 1H), 7.01 (q, J=3.9 Hz, 2H), 4.72 (d, J=13.3 Hz, 1H), 4.36 (dd, J=13.6, 8.3 Hz, 1H), 3.88 (s, 2H), 3.26-3.21 (m, 2H), 3.09 (d, J=12.9 Hz, 1H), 2.16-1.95 (m, 4H), 1.50 (d, J=6.0 Hz, 3H); ESI-MS m/z: 493.1 [M+H]$^+$.

Through the synthesis from different chiral raw materials or separation by chiral SFC, four different optical isomers of compound 1 can be obtained, and the structures are as follows:

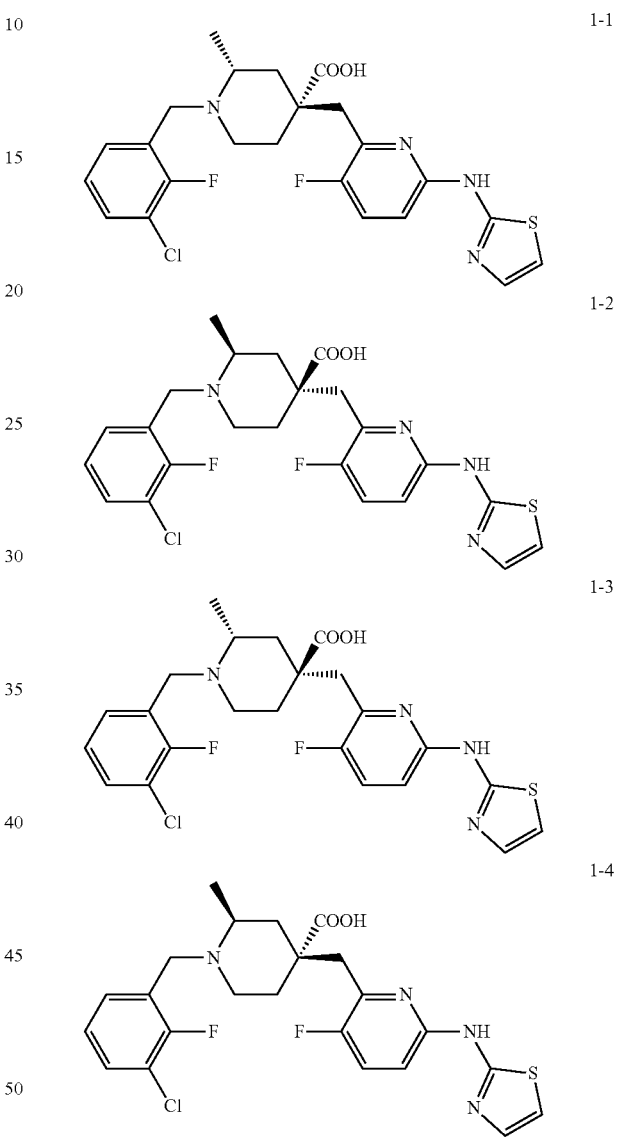

Compounds 1-1, 1-2, 1-3 and 1-4 are designated as follows:
1-1: (2R,4R)-1-(3-chloro-2-fluorobenzyl)-4-((3-fluoro-6-(thiazol-2-ylamino)pyridin-2-yl)methyl)-2-methylpiperidine-4-carboxylic acid;
1-2: (2S,4S)-1-(3-chloro-2-fluorobenzyl)-4-((3-fluoro-6-(thiazol-2-ylamino)pyridin-2-yl)methyl)-2-methylpiperidine-4-carboxylic acid;
1-3: (2R,4S)-1-(3-chloro-2-fluorobenzyl)-4-((3-fluoro-6-(thiazol-2-ylamino)pyridin-2-yl)methyl)-2-methylpiperidine-4-carboxylic acid;
1-4: (2S,4R)-1-(3-chloro-2-fluorobenzyl)-4-((3-fluoro-6-(thiazol-2-ylamino)pyridin-2-yl)methyl)-2-methylpiperidine-4-carboxylic acid.

Other compounds in the present application can also be used to separate the corresponding optical isomers by the same method.

Example 2 Synthesis of 4-((3-fluoro-6-(thiazol-2-ylamino)pyridin-2-yl)methyl)-1-((3-fluoropyridin-4-yl)methyl)-2-methylpiperidine-4-carboxylic acid (compound 2)

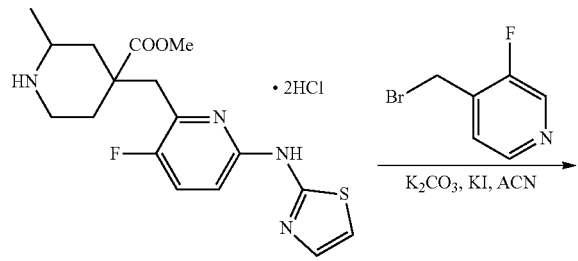

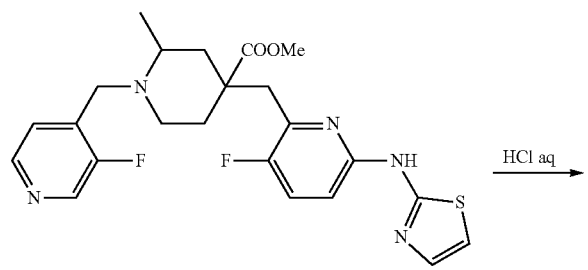

Using methyl 4-((3-fluoro-6-(thiazol-2-ylamino)pyridin-2-yl)methyl)-2-methylpiperidine-4-carboxylate hydrochloride and 4-(bromomethyl)-3-fluoropyridine as starting materials, the target compound was obtained by the same synthetic method in example 1.

$^1$H NMR (400 MHz, DMSO-$d_6$) δ: 12.45 (s, 1H), 11.45 (s, 1H), 8.74 (d, J=1.4 Hz, 1H), 8.54 (d, J=4.9 Hz, 1H), 8.03 (t, J=5.7 Hz, 1H), 7.68 (t, J=9.1 Hz, 1H), 7.50 (d, J=4.0 Hz, 1H), 7.13 (q, J=3.7, 3.3 Hz, 2H), 4.71 (d, J=13.3 Hz, 1H), 4.43 (dd, J=13.5, 7.9 Hz, 1H), 3.93 (s, 1H), 3.39 (dt, J=14.8, 9.1 Hz, 1H), 3.30-3.23 (m, 2H), 3.09 (d, J=13.1 Hz, 1H), 2.08 (t, J=15.2 Hz, 3H), 1.92 (d, J=15.2 Hz, 1H), 1.51 (d, J=6.2 Hz, 3H); ESI-MS m/z: 460.2 [M+H]$^+$.

Example 3 Synthesis of 1-((2-chloro-3-fluoropyridin-4-yl)methyl)-4-((3-fluoro-6-(thiazol-2-ylamino)pyridin-2-yl)methyl)-2-methylpiperidine-4-carboxylic acid (compound 3)

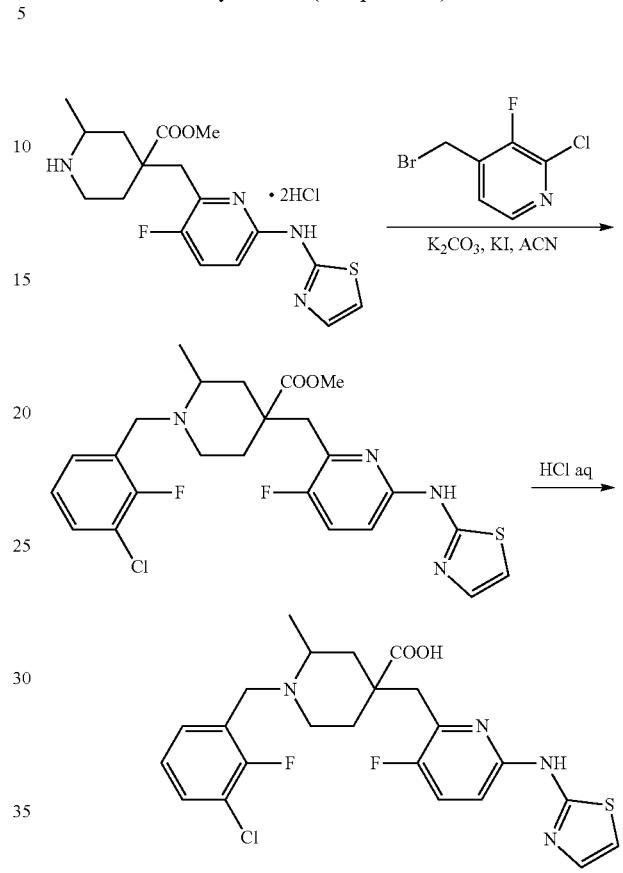

Using methyl 4-((3-fluoro-6-(thiazol-2-ylamino)pyridin-2-yl)methyl)-2-methylpiperidine-4-carboxylate hydrochloride and 4-(bromomethyl)-2-chloro-3-fluoropyridine as starting materials, the target compound was obtained by the same synthetic method in example 1.

$^1$H NMR (400 MHz, DMSO-$d_6$) δ: 11.22 (s, 1H), 9.82 (s, 1H), 8.39 (s, 1H), 7.68 (s, 1H), 7.57 (t, J=9.1 Hz, 1H), 7.37 (d, J=3.6 Hz, 1H), 6.98-6.89 (m, 2H), 4.76 (m, 1H), 4.41 (m, 1H), 3.89 (s, 2H), 3.23 (m, 3H), 2.13 (m, 2H), 1.82 (m, 2H), 1.36 (d, J=6.4 Hz, 3H); ESI-MS m/z: 494.1 [M+H]$^+$.

Example 4 Synthesis of 1-((3-fluoro-2-(2,2,2-trifluoroethoxy)pyridin-4-yl)methyl)-4-((3-fluoro-6-(thiazol-2-ylamino)pyridin-2-yl)methyl)-2-methylpiperidine-4-carboxylic acid (compound 4)

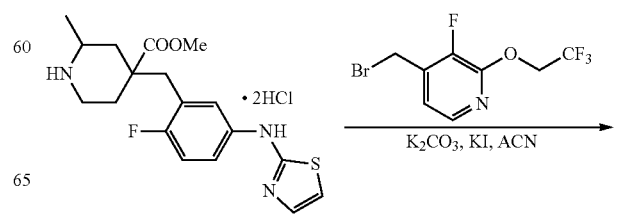

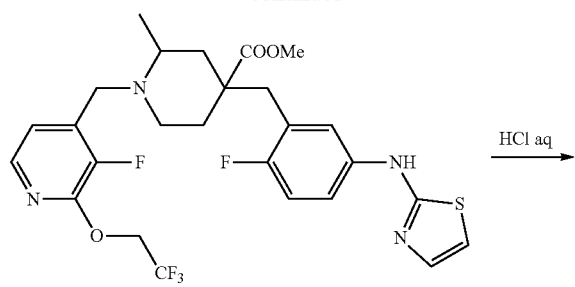

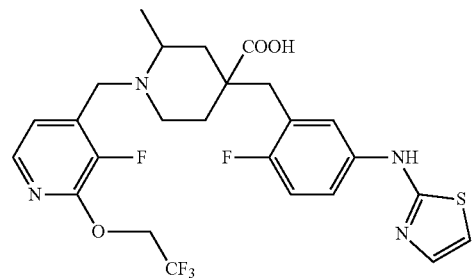

Using methyl 4-((3-fluoro-6-(thiazol-2-ylamino)pyridin-2-yl)methyl)-2-methylpiperidine-4-carboxylate hydrochloride and 4-(bromomethyl)-3-fluoro-2-(2,2,2-trifluoroethoxy)pyridine as starting materials, the target compound was obtained by the same synthetic method in example 1.

$^1$H NMR (400 MHz, Methanol-$d_4$) δ: 7.64 (dd, J=8.3, 7.4 Hz, 1H), 7.32-7.27 (m, 2H), 7.23 (t, J=7.9 Hz, 1H), 7.17 (dd, J=7.8, 1.5 Hz, 1H), 7.02 (d, J=7.2 Hz, 1H), 6.90-6.86 (m, 2H), 3.84-3.77 (m, 2H), 3.73 (s, 2H), 3.44 (t, J=5.1 Hz, 2H), 2.69 (t, J=5.1 Hz, 2H), 2.64-2.58 (m, 3H), 1.53 (d, J=6.0 Hz, 3H); ESI-MS m/z: 558.2 [M+H]$^+$.

Example 5 Synthesis of 1-((5-chlorothiophen-2-yl)methyl)-4-((3-fluoro-6-(thiazol-2-ylamino)pyridin-2-yl)methyl)-2-methylpiperidine-4-carboxylic acid (compound 5)

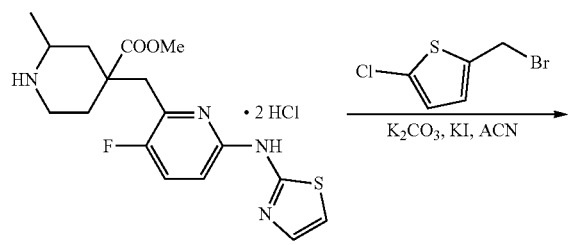

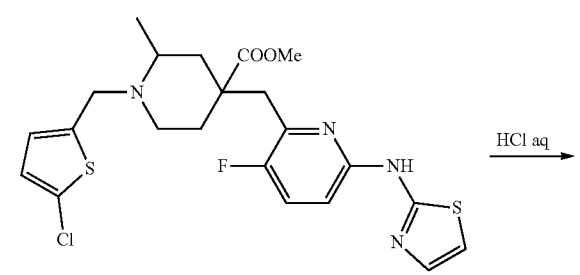

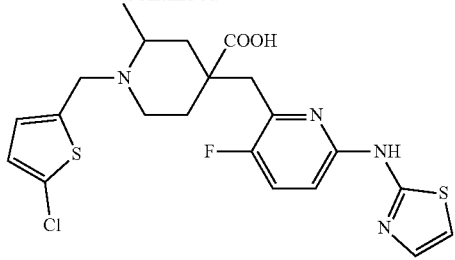

Using methyl 4-((3-fluoro-6-(thiazol-2-ylamino)pyridin-2-yl)methyl)-2-methylpiperidine-4-carboxylate hydrochloride and 2-(bromomethyl)-5-chlorothiophene as starting materials, the target compound was obtained by the same synthetic method in example 1.

$^1$H NMR (400 MHz, Methanol-$d_4$) δ: 7.69 (t, J=8.7 Hz, 1H), 7.58 (s, 1H), 7.25 (q, J=9.5, 7.5 Hz, 2H), 7.15 (dd, J=9.0, 3.0 Hz, 1H), 7.00 (dd, J=30.0, 3.5 Hz, 1H), 4.62-4.37 (m, 2H), 3.80 (d, J=26.4 Hz, 2H), 3.39 (d, J=6.4 Hz, 2H), 3.21-3.11 (m, 1H), 2.33-1.98 (m, 4H), 1.45 (d, J=6.0 Hz, 3H); ESI-MS m/z: 481.1 [M+H]$^+$.

Example 6 Synthesis of 1-(benzofuran-4-ylmethyl)-4-((3-fluoro-6-(thiazol-2-ylamino)pyridin-2-yl)methyl)-2-methylpiperidine-4-carboxylic acid (compound 6)

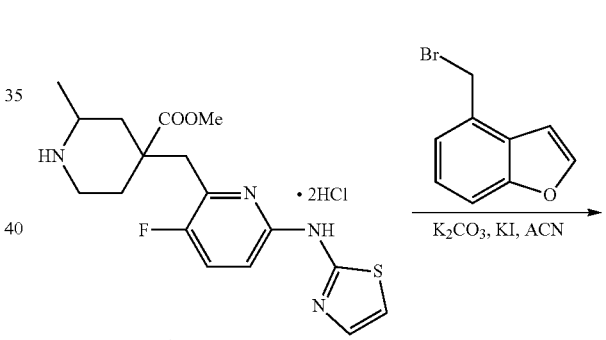

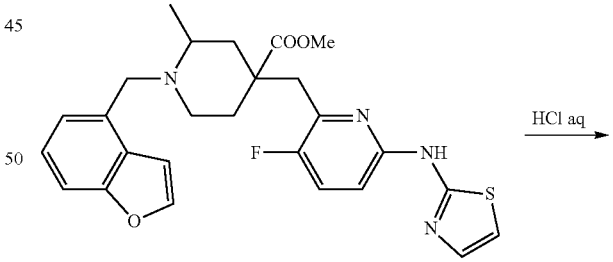

Using methyl 4-((3-fluoro-6-(thiazol-2-ylamino)pyridin-2-yl)methyl)-2-methylpiperidine-4-carboxylate hydrochloride and 4-(bromomethyl)benzofuran as starting materials, the target compound was obtained by the same synthetic method in example 1.

$^1$H NMR (400 MHz, DMSO-d$_6$) δ: 7.62 (d, J=7.2 Hz, 1H), 7.50 (t, J=9.1 Hz, 1H), 7.32 (d, J=3.4 Hz, 1H), 7.24 (dd, J=7.1, 2.1 Hz, 1H), 7.19-7.11 (m, 2H), 6.89 (d, J=5.1 Hz, 2H), 6.65 (d, J=7.2 Hz, 1), 3.84 (d, J=14.1 Hz, 1H), 3.69 (d, J=14.2 Hz, 1H), 3.05 (s, 2H), 2.77-2.73 (m, 1H), 2.65-2.57 (m, 1H), 2.49-2.42 (m, 1H), 1.84-1.75 (m, 1H), 1.72-1.63 (m, 2H), 1.57 (t, J=11.9 Hz, 1H), 1.16 (d, J=6.0 Hz, 3H); ESI-MS m/z: 481.2 [M+H]$^+$.

Example 7 Synthesis of 1-((2,2-difluorobenzo[d][1,3]dioxol-4-yl)methyl)-4-((3-fluoro-6-(thiazol-2-ylamino)pyridin-2-yl)methyl)-2-methylpiperidine-4-carboxylic acid (compound 7)

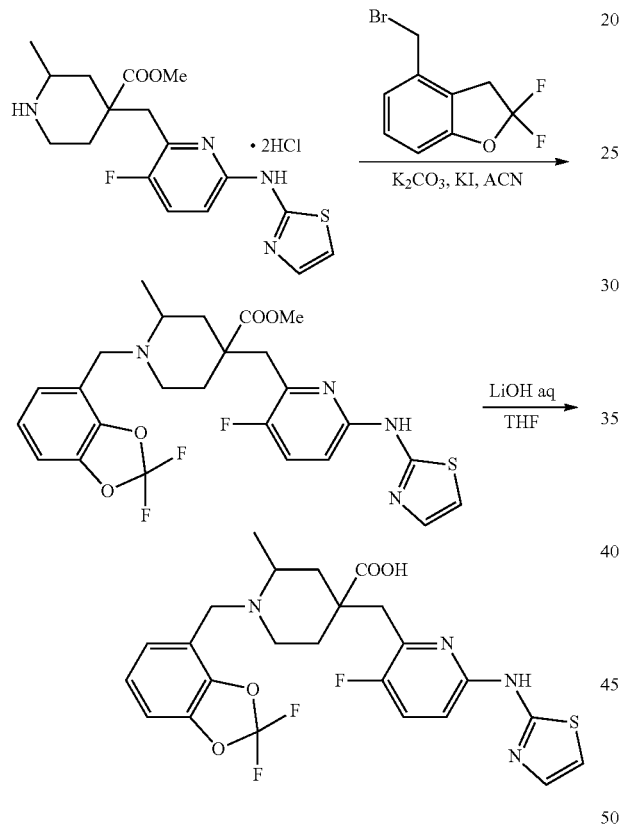

Using methyl 4-((3-fluoro-6-(thiazol-2-ylamino)pyridin-2-yl)methyl)-2-methylpiperidine-4-carboxylate hydrochloride and 4-(bromomethyl)-2,2-difluorobenzo[d][1,3]dioxole as starting materials to get the intermediate methyl 1-((2,2-difluorobenzo[d][1,3]dioxol-4-yl)methyl)-4-((3-fluoro-6-(thiazol-2-ylamino)pyridin-2-yl)methyl)-2-methylpiperidine-4-carboxylate.

The abovementioned intermediate added to a 100 mL flask, followed by adding THF (10 mL), H$_2$O (5 mL) and LiOH·H$_2$O (79 mg, 1.88 mmol), then heated to 60° C. and stirred for 5 h under the protection of Ar. After the completion of the reaction determined by LC-MS, it was concentrated to the volume about 7.5 mL, the residual was purified by reverse phase flash to obtain the target compound (60 mg, yield 62%).

$^1$H NMR (400 MHz, DMSO-d$_6$) δ: 7.50 (t, J=9.1 Hz, 1H), 7.32 (d, J=3.4 Hz, 1H), 7.24 (dd, J=7.1, 2.1 Hz, 1H), 7.19-7.11 (m, 2H), 6.89 (d, J=5.1 Hz, 2H), 3.94 (d, J=14.1 Hz, 1H), 3.39 (d, J=14.2 Hz, 1H), 3.05 (s, 2H), 2.75-2.71 (m, 1H), 2.61-2.52 (m, 1H), 2.45-2.40 (m, 1H), 1.83-1.79 (m, 1H), 1.75-1.62 (m, 2H), 1.54 (t, J=11.9 Hz, 1H), 1.06 (d, J=6.0 Hz, 3H); ESI-MS m/z: 521.2 [M+H]$^+$.

Example 8 Synthesis of 1-((2,2-difluoro-2,3-dihydro-1H-inden-4-yl)methyl)-4-((3-fluoro-6-(thiazol-2-ylamino)pyridin-2-yl)methyl)-2-methylpiperidine-4-carboxylic acid (compound 8)

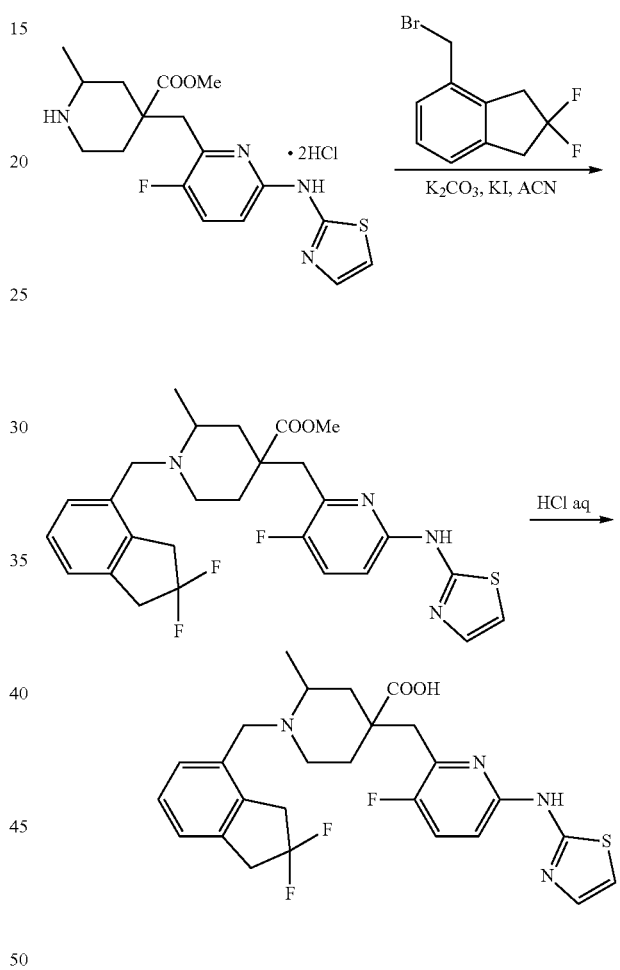

Using methyl 4-((3-fluoro-6-(thiazol-2-ylamino)pyridin-2-yl)methyl)-2-methylpiperidine-4-carboxylate hydrochloride and 4-(bromomethyl)-2,2-difluoro-2,3-dihydro-1H-indene as starting materials, the target compound was obtained by the same synthetic method in example 1.

$^1$H NMR (400 MHz, DMSO-d$_6$) δ: 7.52 (t, J=9.1 Hz, 1H), 7.30 (d, J=3.4 Hz, 1H), 7.23 (dd, J=7.1, 2.1 Hz, 1H), 7.19-7.11 (m, 2H), 6.89 (d, J=5.0 Hz, 2H), 5.34-5.21 (m, 4H), 3.94 (d, J=14.1 Hz, 1H), 3.39 (d, J=14.2 Hz, 1H), 3.05 (s, 2H), 2.75-2.71 (m, 1H), 2.61-2.50 (m, 1H), 2.45-2.40 (m, 1H), 1.83-1.79 (m, 1H), 1.75-1.65 (m, 2H), 1.54 (t, J=11.9 Hz, 1H), 1.07 (d, J=6.0 Hz, 3H); ESI-MS m/z: 517.2 [M+H]$^+$.

Example 9 Synthesis of 1-(1-(3-chloro-2-fluorophenyl)ethyl)-4-((3-fluoro-6-(thiazol-2-ylamino)pyridin-2-yl)methyl)-2-methylpiperidine-4-carboxylic acid (compound 9)

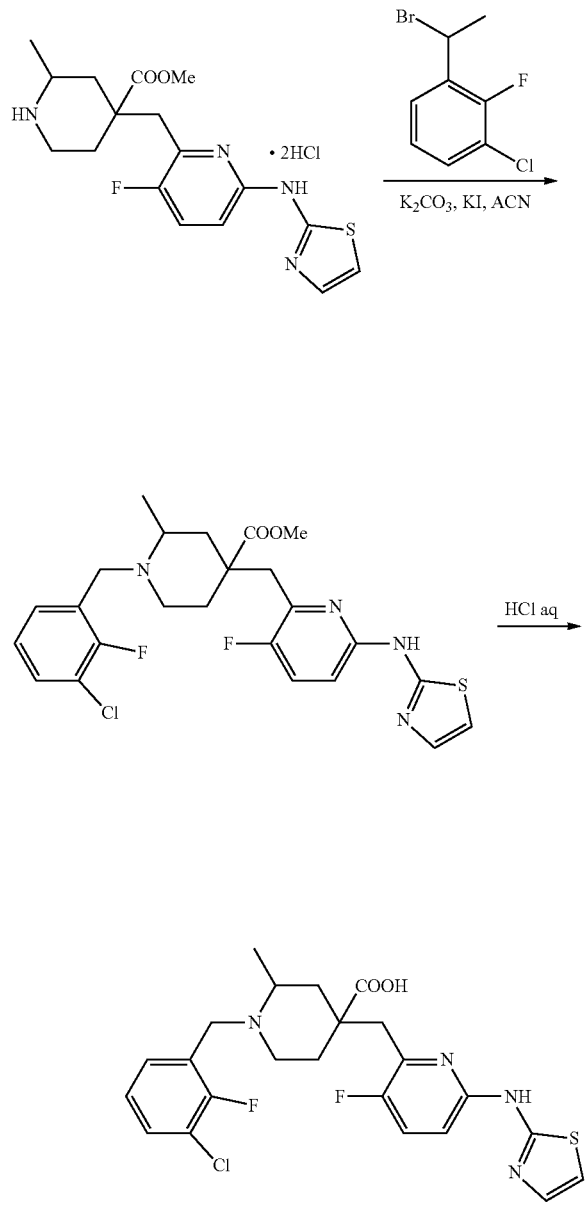

Using methyl 4-((3-fluoro-6-(thiazol-2-ylamino)pyridin-2-yl)methyl)-2-methylpiperidine-4-carboxylate hydrochloride and 1-(1-bromoethyl)-3-chloro-2-fluorobenzene as starting materials, the target compound was obtained by the same synthetic method in example 1.

$^1$H NMR (400 MHz, DMSO-$d_6$) δ: 12.27 (s, 1H), 11.15 (s, 1H), 7.55 (d, J=8.1 Hz, 1H), 7.49-7.34 (m, 2H), 7.18 (t, J=7.8 Hz, 1H), 7.02 (s, 1H), 6.86 (d, J=8.3 Hz, 1H), 6.67 (d, J=7.3 Hz, 1H), 4.41 (m, 1H), 3.11 (d, J=16.6 Hz, 2H), 3.02 (m, 2H), 2.85 (m, 1H), 1.76-1.52 (m, 4H), 1.30 (d, J=6.7 Hz, 3H), 1.06 (q, J=7.1, 6.4 Hz, 3H); ESI-MS m/z: 507.2 [M+H]$^+$.

Example 10 Synthesis of 1-(1-(3-chloro-2-fluorophenyl)cyclopropyl)-4-((3-fluoro-6-(thiazol-2-ylamino)pyridin-2-yl)methyl)-2-methylpiperidine-4-carboxylic acid (compound 10)

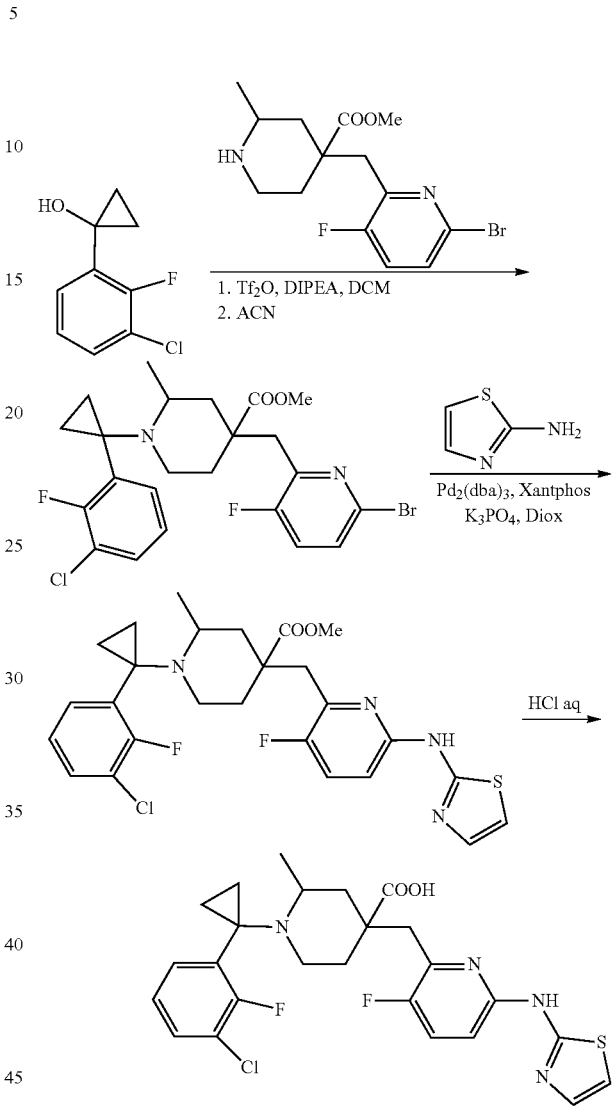

Methyl 4-((6-bromo-3-fluoropyridin-2-yl)methyl)-1-(1-(3-chloro-2-fluorophenyl)-cyclopropyl)-2-methylpiperidine-4-carboxylate 1-(3-chloro-2-fluorophenyl)cyclopropan-1-ol (400 mg, 2.145 mmol) was added to a 100 mL flask, followed by adding dry DCM (10 mL) and DIPEA (692 mg, 5.362 mmol), cooled to −45° C. under Ar protection, then added Tf$_2$O (726 mg, 2.574 mmol, in 10 mL DCM), the mixture was stirred 2 h under-50 to −40° C. Methyl 4-((6-bromo-3-fluoropyridin-2-yl)methyl)-2-methylpiperidine-4-carboxylate (444 mg, 1.287 mmol, in 10 mL CH$_3$CN) was added, increased the temperature to room temperature and stirred for 2 h. After the completion of the reaction determined by LC-MS, it was quenched with water (20 mL), separated the organic phase, extracted with DCM (20 mL), combined the organic phase and concentrated, the residual was purified by column chromatography to obtain the target compound (284 mg, yield 43%), ESI-MS m/z: 533.2 [M+H]$^+$.

1-(1-(3-chloro-2-fluorophenyl)cyclopropyl)-4-((3-fluoro-6-(thiazol-2-ylamino)pyridin-2-yl)methyl)-2-methylpiperidine-4-carboxylic acid Using Methyl 4-((6-bromo-3-fluoropyridin-2-yl)methyl)-1-(1-(3-chloro-2-fluorophenyl)cyclopropyl)-2-methylpiperidine-4-carboxylate as starting materials, the target compound was obtained by the same synthetic method in example 1.

$^1$H NMR (400 MHz, DMSO-$d_6$) δ: 12.11 (s, 1H), 11.02 (s, 1H), 7.57 (d, J=8.1 Hz, 1H), 7.43-7.33 (m, 2H), 7.15 (t, J=7.8 Hz, 1H), 7.02 (s, 1H), 6.84 (d, J=8.3 Hz, 1H), 6.65 (d, J=7.3 Hz, 1H), 3.41 (d, J=16.6 Hz, 2H), 3.02 (m, 3H), 2.23-1.89 (m, 4H), 1.30 (d, J=6.7 Hz, 3H), 0.75-0.62 (m, 4H); ESI-MS m/z: 519.2 [M+H]$^+$.

Example 11 Synthesis of 1-(3-(3-chloro-2-fluorophenyl) oxetan-3-yl)-4-((3-fluoro-6-(thiazol-2-ylamino)pyridin-2-yl)methyl)-2-methylpiperidine-4-carboxylic acid (compound 11)

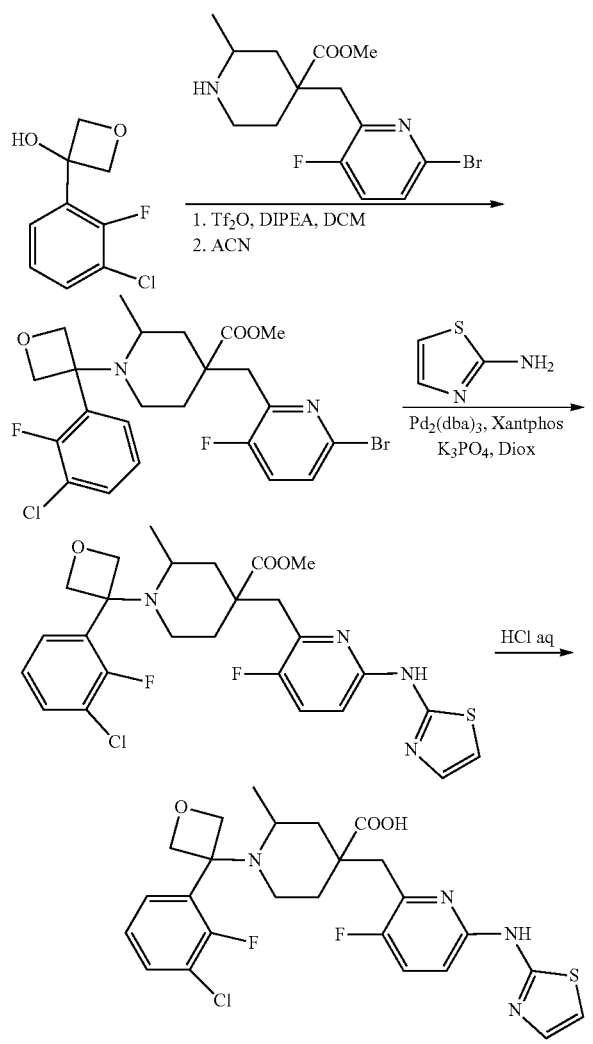

Using methyl 4-((6-bromo-3-fluoropyridin-2-yl)methyl)-2-methylpiperidine-4-carboxylate and 3-(3-chloro-2-fluorophenyl) oxetan-3-ol as starting materials, intermediate methyl 4-((6-bromo-3-fluoropyridin-2-yl)methyl)-1-(3-(3-chloro-2-fluorophenyl) oxetan-3-yl)-2-methylpiperidine-4-carboxylate was obtained by the same synthetic method in example 10.

Using abovementioned intermediate and thiazol-2-amine as starting materials, the target compound was obtained by the same synthetic method in example 1.

$^1$H NMR (400 MHz, CD$_3$OD) δ: 7.46 (m, 2H), 7.35-7.16 (m, 3H), 6.93 (dt, J=8.9, 3.3 Hz, 1H), 6.87 (t, J=4.1 Hz, 1H), 4.77 (s, 1H), 4.70-4.47 (m, 2H), 4.31 (d, J=12.2 Hz, 1H), 4.14 (d, J=8.0 Hz, 1H), 3.98 (ab, J=29.9, 12.4 Hz, 1H), 3.67 (t, J=11.3 Hz, 1H), 3.17-2.96 (m, 2H), 2.50-2.13 (m, 3H), 2.08-1.95 (m, 1H), 1.89 (d, J=12.4 Hz, 1H), 1.41 (d, J=6.9 Hz, 3H); ESI-MS m/z: 535.2 [M+H]$^+$.

Example 12 Synthesis of 1-(3-chloro-2-fluorobenzoyl)-4-((3-fluoro-6-(thiazol-2-ylamino)pyridin-2-yl)methyl)-2-methylpiperidine-4-carboxylic acid (compound 12)

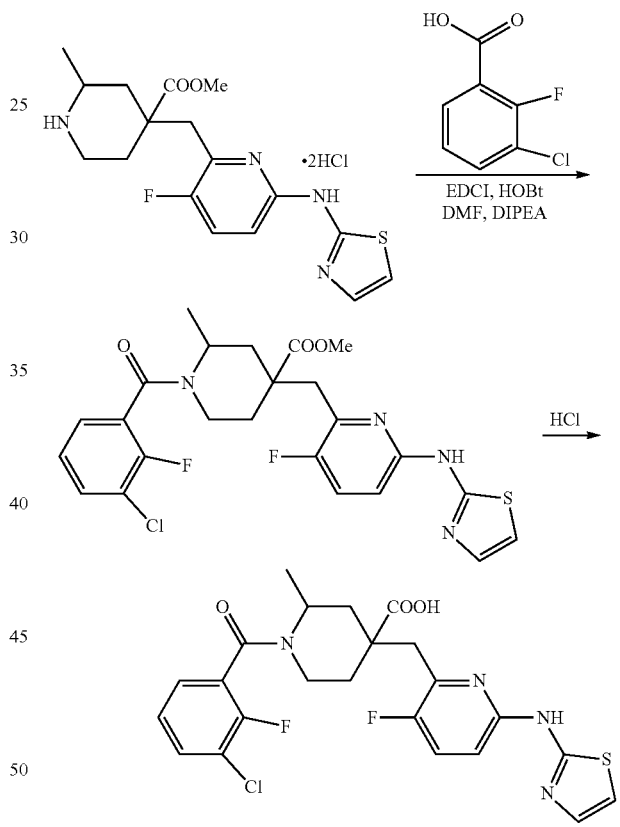

3-Chloro-2-fluorobenzoic acid (262 mg, 1.50 mmol), DMF (20 mL), EDCI (431 mg, 2.25 mmol), HOBt (304 mg, 2.25 mmol) and DIPEA (970 mg, 7.52 mmol) was added to a 100 mL flask, the mixture was stirred at room temperature for 30 min under the protection of Ar, methyl 4-((3-fluoro-6-(thiazol-2-ylamino)pyridin-2-yl)methyl)-2-methylpiperidine-4-carboxylate hydrochloride (437 mg, 1.0 mmol) was added, then stirred at room temperature for 20 h, After the completion of the reaction determined by LC-MS, quenched with water (40 mL), exacted with EA (50 mL*2), combined with the organic phase and washed with saturated NaCl solution, concentrated, the residual was purified by column chromatography to obtain the desired intermediate (365 mg, yield 70%).

Using abovementioned intermediate as starting materials, the target compound was obtained by the same synthetic method in example 1.

¹H NMR (400 MHz, CD₃OD) δ: 7.68 (t, J=9.0 Hz, 1H), 7.62-7.52 (m, 2H), 7.43 (dt, J=12.0, 7.9 Hz, 1H), 7.27 (d, J=7.5 Hz, 1H), 7.21 (d, J=4.3 Hz, 1H), 7.12 (dd, J=8.9, 3.0 Hz, 1H), 3.73 (s, 2H), 3.22-3.12 (m, 3H), 2.13-1.88 (m, 4H), 1.45 (d, J=6.0 Hz, 3H); ESI-MS m/z: 475.2 [M+H]⁺.

Example 13 Synthesis of 1-((3-chloro-2-fluorophenyl)methyl-d₂)-4-((3-fluoro-6-(thiazol-2-ylamino)pyridin-2-yl)methyl)-2-methylpiperidine-4-carboxylic acid (compound 13)

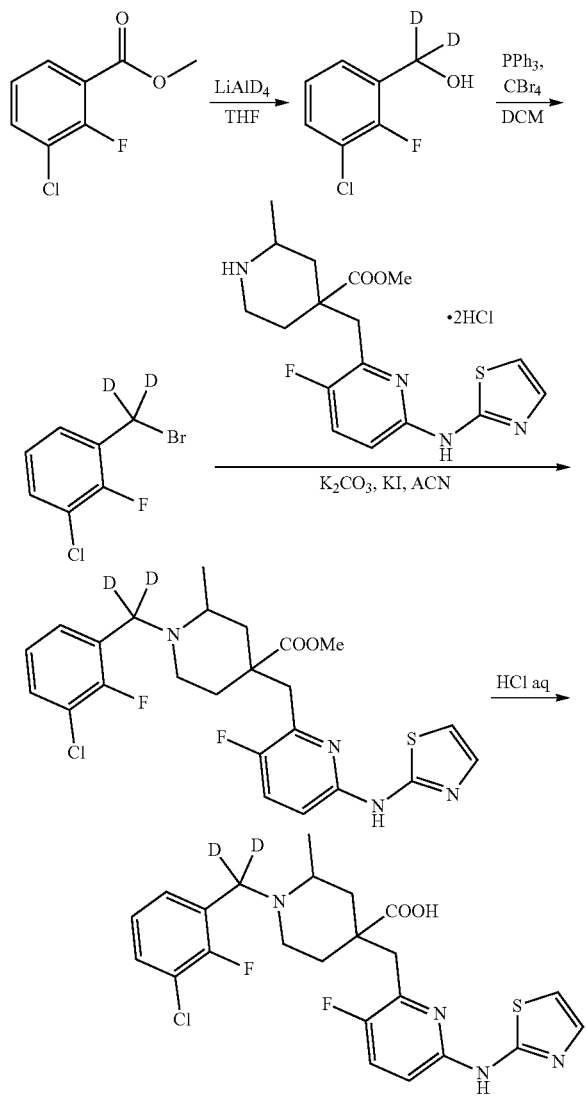

1-(Bromomethyl-d₂)-3-chloro-2-fluorobenzene

Methyl 3-chloro-2-fluorobenzoate (658 mg, 3.49 mmol) and THF (dry, 10 mL) was added to a 100 mL flask, LiAlD₄ (146 mg, 3.49 mmol) was added dropwise under ice-bath, further stirred about 0.5 h. After the completion of the reaction based on TLC (PE/EA=10/1), quenched with water (20 mL) under ice-bath, saturated NaCl solution (20 mL) was added, exacted with EA (20 mL*2), combined the organic phase and dried over anhydrous sodium sulfate, filtered and concentrated to obtained crude intermediate (3-chloro-2-fluorophenyl) methan-d₂-ol, which was used to the next step without further purification.

(3-chloro-2-fluorophenyl) methan-d₂-ol, DCM (20 mL) and CBr₄ (2 g, 6.03 mmol) was added to a 100 mL flask, PPh₃ (1.371 g, 5.23 mmol) was added dropwise, stirred at room temperature for about 1 h. After the completion of the reaction determined by TLC (PE/EA=10/1), concentrated and the residual was purified by column chromatography (PE, 800 mL) to obtain 1-(bromomethyl-d₂)-3-chloro-2-fluorobenzene as colorless liquid (921 mg, yield 100%).

¹H NMR (400 MHz, CDCl₃) δ 7.34 (ddd, J=8.3, 6.9, 1.7 Hz, 1H), 7.27 (ddd, J=7.9, 6.5, 1.7 Hz, 1H), 7.05 (td, J=7.9, 1.2 Hz, 1H).

Methyl 1-((3-chloro-2-fluorophenyl)methyl-d₂)-4-((3-fluoro-6-(thiazol-2-ylamino) pyri-din-2-yl)methyl)-2-methylpiperidine-4-carboxylate Methyl 4-((3-fluoro-6-(thiazol-2-ylamino)pyridin-2-yl)methyl)-2-methylpiperidine-4-carboxylate hydrochloride (800 mg, 1.83 mmol), 1-(bromomethyl-d₂)-3-chloro-2-fluorobenzene (495 mg, 2.19 mmol), K₂CO₃ (1.264 g, 9.15 mmol), KI (20 mg) and ACN (20 mL) was added to a 100 mL flask, stirred at room temperature for about 2 h. After the completion of the reaction determined by TLC, water (100 mL) was added to precipitate the solid, followed by filtration. The filter cake was washed twice with water (20 mL*2) and then slurried with PE (50 mL). After filtration, the filter cake was washed with PE (20 mL*2) and dried to obtain the crude product methyl 1-((3-chloro-2-fluorophenyl)methyl-d₂)-4-((3-fluoro-6-(thiazol-2-ylamino)pyridin-2-yl)methyl)-2-methylpiperidine-4-carboxylate (931 mg, yield 100%), which was used to the next step without further purification. ESI-MS m/z: 509.2 [M+H]⁺.

1-((3-chloro-2-fluorophenyl)methyl-d₂)-4-((3-fluoro-6-(thiazol-2-ylamino)pyridin-2-yl)methyl)-2-methylpiperidine-4-carboxylic acid Methyl 1-((3-chloro-2-fluorophenyl)methyl-d₂)-4-((3-fluoro-6-(thiazol-2-ylamino)-pyridin-2-yl)methyl)-2-methylpiperidine-4-carboxylate (931 mg, 1.83 mmol) was added to a 100 mL flask, then water (15 mL) and con. HCl (15 mL) was added, heated to 105° C. under refluxing temperature and further reacted for 5 h. After the completion of the reaction determined by LC-MS, it was concentrated and the residual was slurried with ACN (30 mL) at room temperature. After filtration, the filter cake was washed with ACN (5 mL*2), and dried to obtain the desired target compound as yellow powder (815 mg, yield 90%).

¹H NMR (400 MHz, CD₃OD) δ: 7.73 (t, J=8.7 Hz, 1H), 7.70-7.55 (m, 3H), 7.36-7.24 (m, 2H), 7.20 (dd, J=8.8, 2.9 Hz, 1H), 3.96 (s, 2H), 3.57-3.44 (m, 2H), 3.36 (s, 1H), 2.41-1.96 (m, 4H), 1.53 (m, 3H); ESI-MS m/z: 495.1 [M+H]⁺.

Through the synthesis from different chiral raw materials or separation by chiral SFC, four different optical isomers of compound 13 can be obtained, and the structures are as follows:

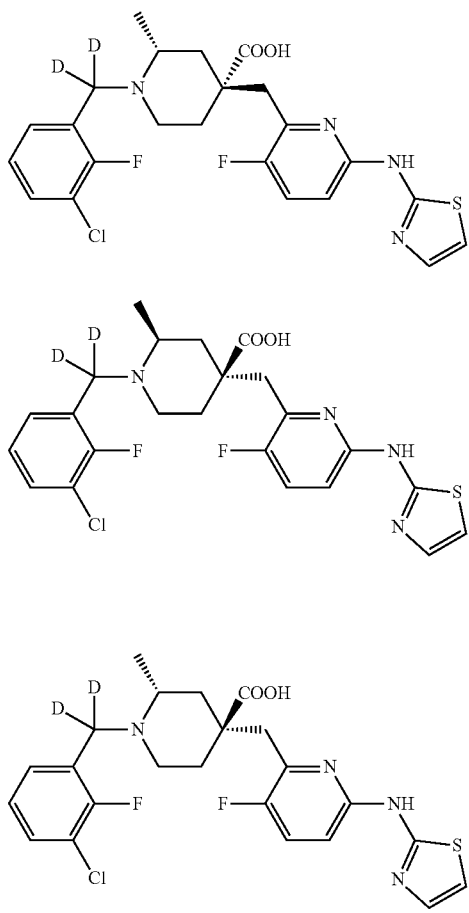

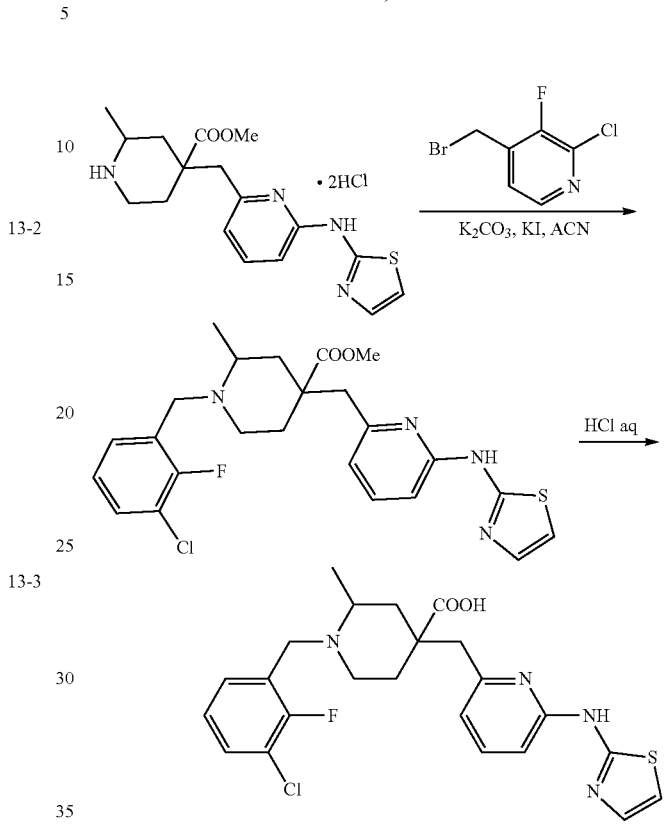

Compounds 13-1, 13-2, 13-3 and 13-4 are designated as follows:

13-1: (2R,4R)-1-((3-chloro-2-fluorophenyl)methyl-d₂)-4-((3-fluoro-6-(thiazol-2-ylamino)pyridin-2-yl)methyl)-2-methylpiperidine-4-carboxylic acid;

13-2: (2S,4S)-1-((3-chloro-2-fluorophenyl)methyl-d₂)-4-((3-fluoro-6-(thiazol-2-ylamino)pyridin-2-yl)methyl)-2-methylpiperidine-4-carboxylic acid;

13-3: (2R,4S)-1-((3-chloro-2-fluorophenyl)methyl-d₂)-4-((3-fluoro-6-(thiazol-2-ylamino)pyridin-2-yl)methyl)-2-methylpiperidine-4-carboxylic acid;

13-4: (2S,4R)-1-((3-chloro-2-fluorophenyl)methyl-d₂)-4-((3-fluoro-6-(thiazol-2-ylamino)pyridin-2-yl)methyl)-2-methylpiperidine-4-carboxylic acid.

Example 14 Synthesis of 1-(3-chloro-2-fluorobenzyl)-2-methyl-4-((6-(thiazol-2-ylamino)pyridin-2-yl)methyl) piperidine-4-carboxylic acid (compound 14)

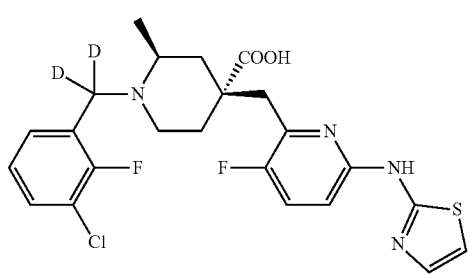

Using methyl 4-((3-fluoro-6-(thiazol-2-ylamino)pyridin-2-yl)methyl)-2-methylpiperidine-4-carboxylate hydrochloride and 1-(bromomethyl)-3-chloro-2-fluorobenzene as starting materials, the target compound was obtained by the same synthetic method in example 1.

$^1$H NMR (400 MHz, DMSO-d$_6$) δ: 11.88 (s, 1H), 10.79 (s, 1H), 7.74 (t, J=7.2 Hz, 1H), 7.72-7.63 (m, 2H), 7.55 (t, J=9.2 Hz, 1H), 7.41 (d, J=3.7 Hz, 1H), 7.32 (t, J=7.9 Hz, 1H), 7.06 (q, J=3.9 Hz, 2H), 4.73 (d, J=13.3 Hz, 1H), 4.38 (dd, J=13.6, 8.3 Hz, 1H), 3.68 (s, 2H), 3.26-3.24 (m, 2H), 3.02 (d, J=12.9 Hz, 1H), 2.15-1.91 (m, 4H), 1.52 (d, J=6.0 Hz, 3H); ESI-MS m/z: 507.1 [M+H]$^+$.

Example 15 Synthesis of 1-((3-chloro-2-fluorophenyl)methyl-d₂)-2-methyl-4-((6-(thiazol-2-ylamino)pyridin-2-yl)methyl) piperidine-4-carboxylic acid (compound 15)

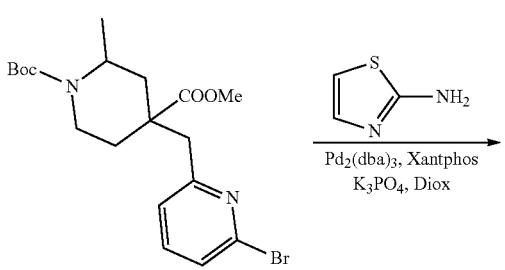

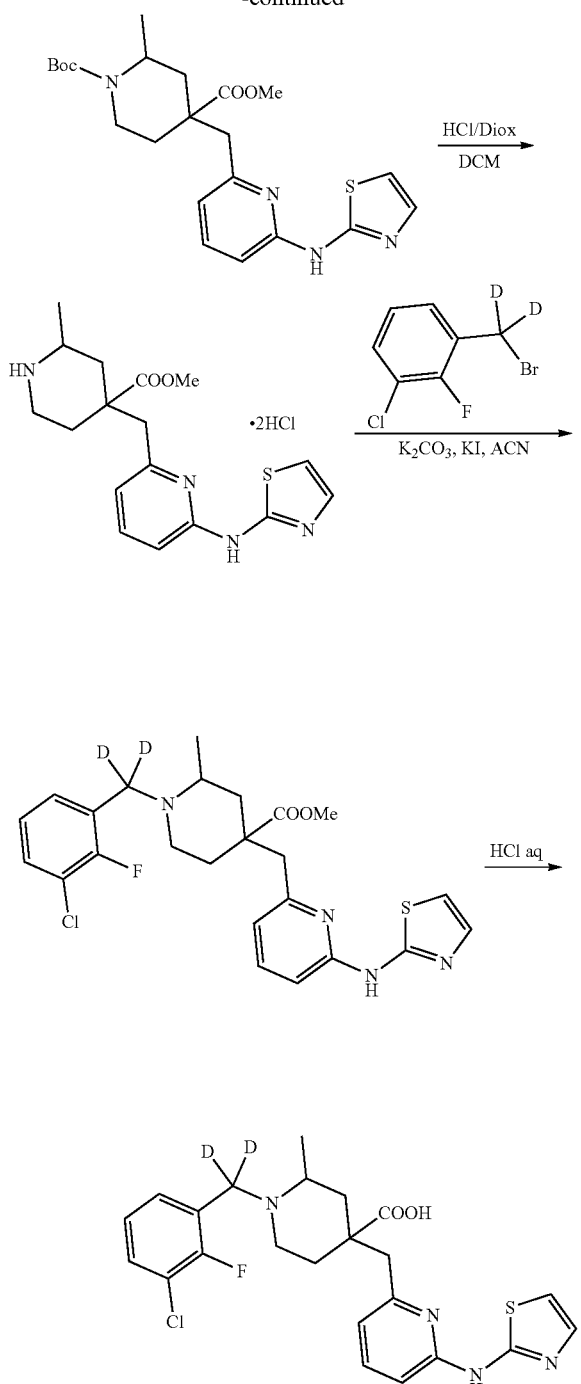

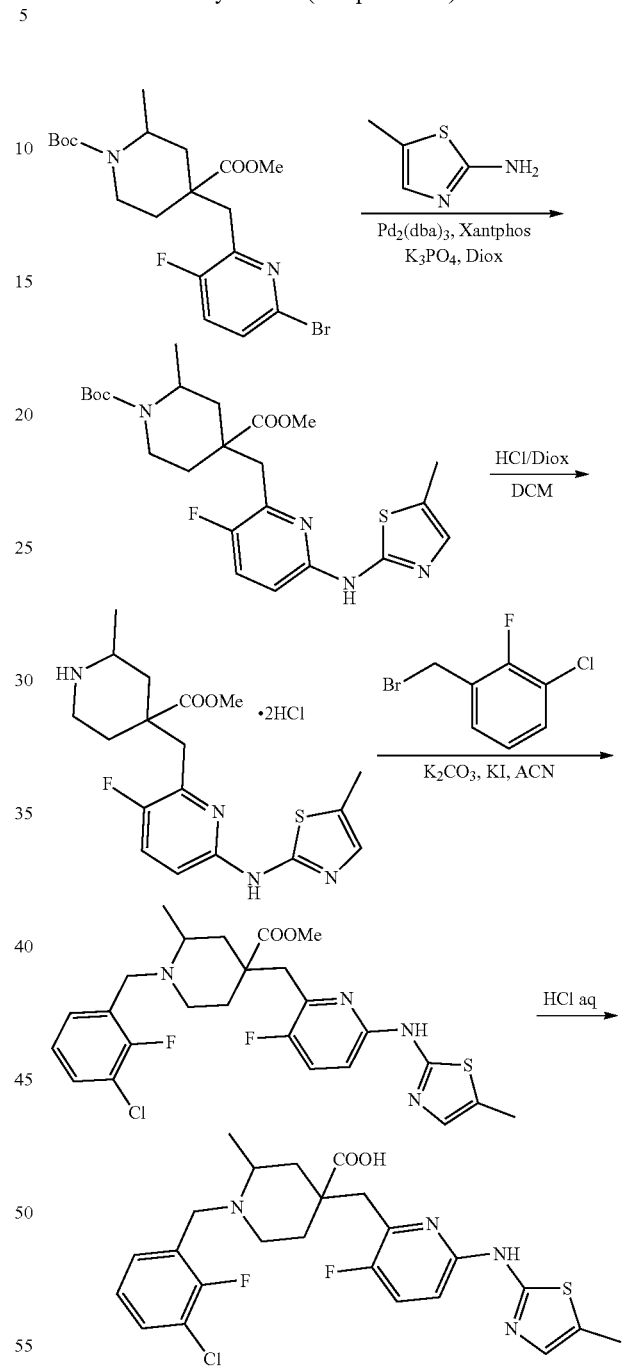

Example 16 Synthesis of 1-(3-chloro-2-fluorobenzyl)-4-((3-fluoro-6-((5-methylthiazol-2-yl)amino)pyridin-2-yl)methyl)-2-methylpiperidine-4-carboxylic acid (compound 16)

Using methyl 1-(tert-butyl) 4-methyl 4-((6-bromo-3-fluoropyridin-2-yl)methyl)-2-methylpiperidine-1,4-dicarboxylate and thiazol-2-amine as starting materials, the target compound was obtained by the same synthetic method in example 1.

$^1$H NMR (400 MHz, CD$_3$OD) δ: 7.78 (t, J=8.7 Hz, 1H), 7.70-7.55 (m, 3H), 7.36-7.24 (m, 3H), 7.23 (dd, J=8.8, 2.9 Hz, 1H), 3.92 (s, 2H), 3.57-3.44 (m, 2H), 3.36 (m, 1H), 2.41-1.96 (m, 4H), 1.55 (m, 3H); ESI-MS m/z: 477.1 [M+H]$^+$.

Using 1-(tert-butyl) 4-methyl 4-((6-bromo-3-fluoropyridin-2-yl)methyl)-2-methylpiperidine-1,4-dicarboxylate and 5-methylthiazol-2-amine as starting materials, the target compound was obtained by the same synthetic method in example 1.

$^1$H NMR (400 MHz, DMSO-d$_6$) δ: 11.66 (s, 1H), 10.59 (s, 1H), 7.76 (t, J=7.2 Hz, 1H), 7.72-7.66 (m, 2H), 7.55 (t, J=9.2 Hz, 1H), 7.34 (t, J=7.9 Hz, 1H), 7.01 (m, 1H), 4.72 (d, J=13.3 Hz, 1H), 4.36 (dd, J=13.6, 8.3 Hz, 1H), 3.88 (s, 2H), 3.26-3.21 (m, 2H), 3.09 (d, J=12.9 Hz, 1H), 2.27 (s, 3H), 2.16-1.95 (m, 4H), 1.50 (d, J=6.0 Hz, 3H); ESI-MS m/z: 508.1 [M+H]+.

Example 17 Synthesis of 1-((3-chloro-2-fluorophenyl)methyl-d₂)-4-((3-fluoro-6-((5-methylthiazol-2-yl)amino)pyridin-2-yl)methyl)-2-methylpiperidine-4-carboxylic acid (compound 17)

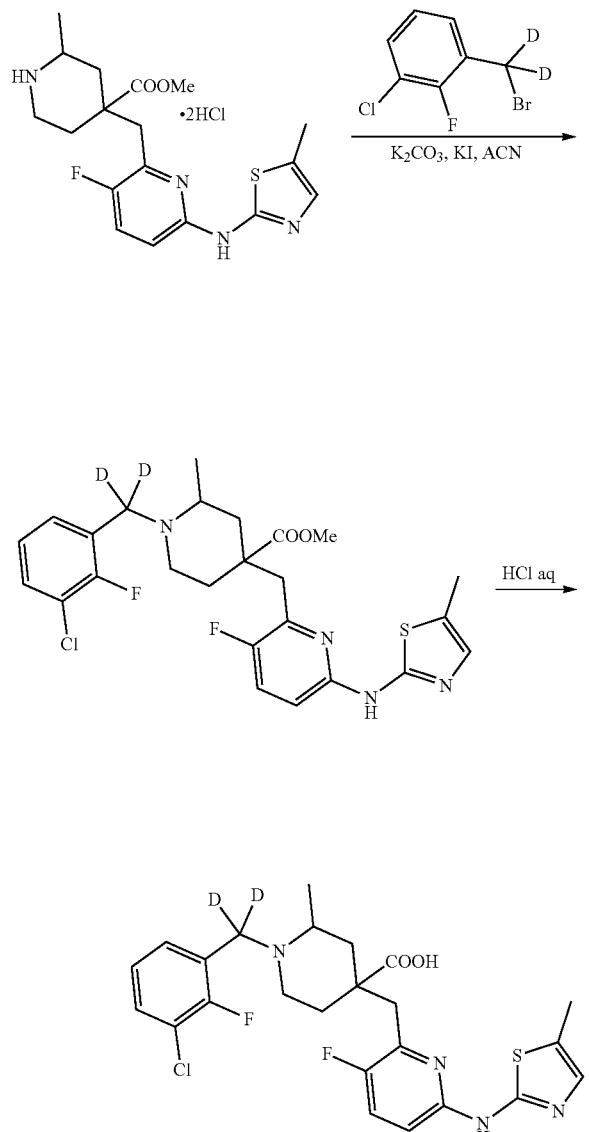

Using methyl 4-((3-fluoro-6-(thiazol-2-ylamino)pyridin-2-yl)methyl)-2-methylpiperidine-4-carboxylate hydrochloride and 1-(bromomethyl-d₂)-3-chloro-2-fluorobenzene as starting materials, the target compound was obtained by the same synthetic method in example 1.

¹H NMR (400 MHz, CD₃OD) δ: 7.75 (t, J=8.7 Hz, 1H), 7.72-7.56 (m, 3H), 7.28 (s, 1H), 7.20 (dd, J=8.8, 2.9 Hz, 1H), 3.96 (s, 2H), 3.57-3.44 (m, 2H), 3.36 (s, 1H), 2.57 (s, 3H), 2.41-1.96 (m, 4H), 1.53 (m, 3H); ESI-MS m/z: 510.0 [M+H]+.

Example 18 Synthesis of 1-(3-chloro-2-fluorobenzyl)-4-((3-fluoro-6-((4-methylthiazol-2-yl)amino)pyridin-2-yl)methyl)-2-methylpiperidine-4-carboxylic acid (compound 18)

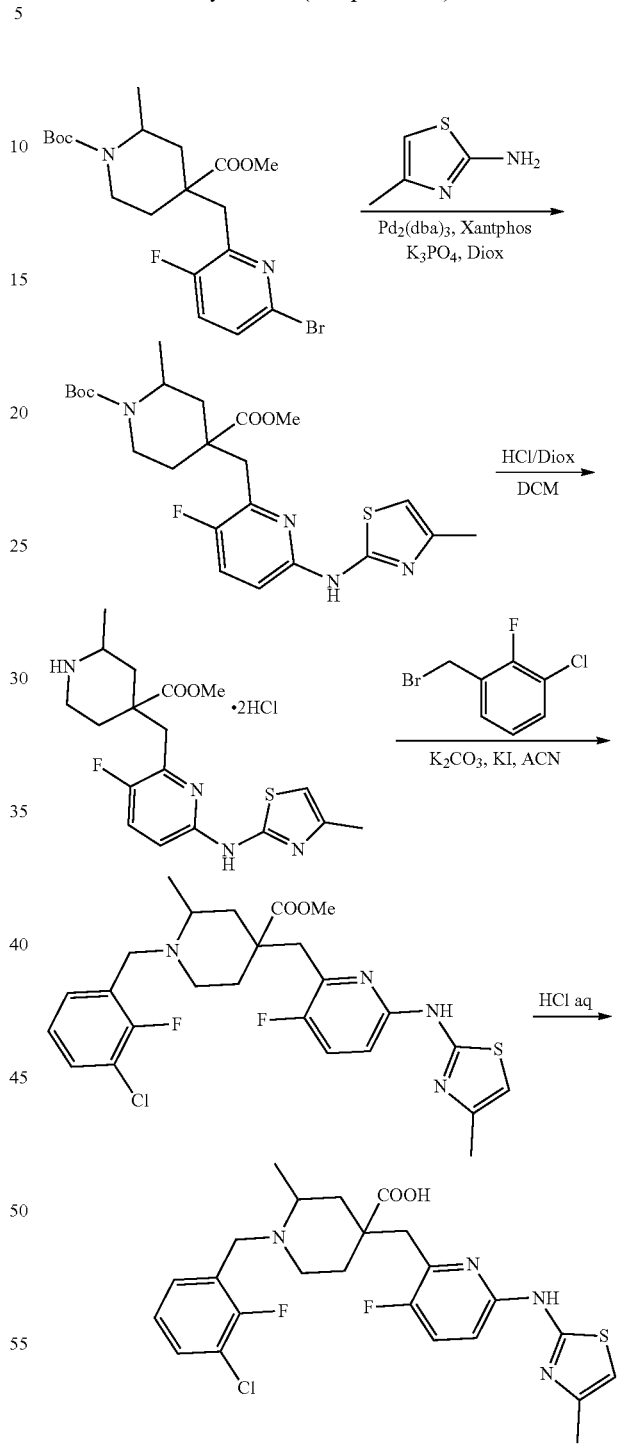

Using 1-(tert-butyl) 4-methyl 4-((6-bromo-3-fluoropyridin-2-yl)methyl)-2-methylpiperidine-1,4-dicarboxylate and 4-methylthiazol-2-amine as starting materials, the target compound was obtained by the same synthetic method in example 1.

¹H NMR (400 MHz, DMSO-d₆) δ: 11.64 (s, 1H), 10.53 (s, 1H), 7.73 (t, J=7.2 Hz, 1H), 7.70-7.66 (m, 2H), 7.55 (t, J=9.2

Hz, 1H), 7.34 (t, J=7.9 Hz, 1H), 6.56 (s, 1H), 4.68 (d, J=13.3 Hz, 1H), 4.37 (dd, J=13.6, 8.3 Hz, 1H), 3.83 (s, 2H), 3.26-3.21 (m, 2H), 3.06 (d, J=12.9 Hz, 1H), 2.17 (s, 3H), 2.14-1.93 (m, 4H), 1.51 (d, J=6.0 Hz, 3H); ESI-MS m/z: 508.1 [M+H]⁺.

Example 19 Synthesis of 1-((3-chloro-2-fluorophenyl)methyl-d₂)-4-((3-fluoro-6-((4-methylthiazol-2-yl)amino)pyridin-2-yl)methyl)-2-methylpiperidine-4-carboxylic acid (compound 19)

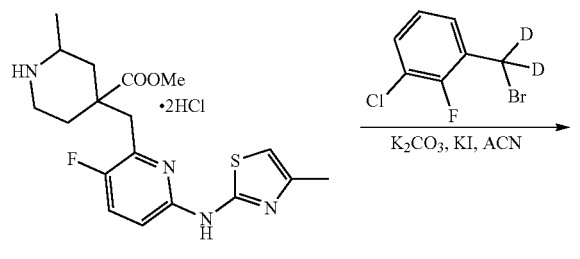

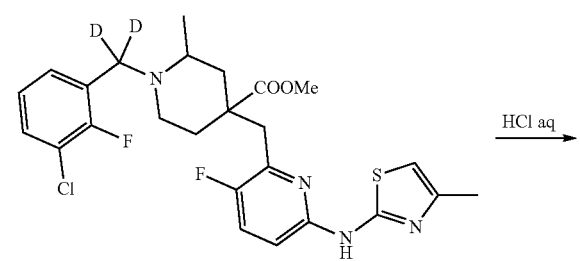

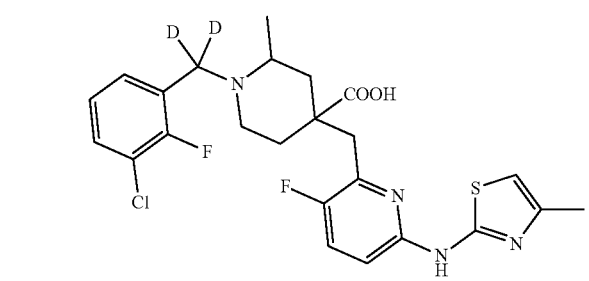

Using methyl 4-((3-fluoro-6-(thiazol-2-ylamino)pyridin-2-yl)methyl)-2-methylpiperidine-4-carboxylate hydrochloride and 1-(bromomethyl-d₂)-3-chloro-2-fluorobenzene as starting materials, the target compound was obtained by the same synthetic method in example 1.

¹H NMR (400 MHz, CD₃OD) δ: 7.76 (t, J=8.7 Hz, 1H), 7.73-7.57 (m, 3H), 7.22 (dd, J=8.8, 2.9 Hz, 1H), 6.58 (s, 1H), 3.92 (s, 2H), 3.44-3.31 (m, 2H), 3.16 (m, 1H), 2.19 (s, 3H), 2.15-1.86 (m, 4H), 1.51 (m, 3H); ESI-MS m/z: 510.0 [M+H]⁺.

Example 20 Synthesis of 1-(3-chloro-2-fluorobenzyl)-4-((3-fluoro-6-(thiazol-2-ylamino)pyridin-2-yl)methyl)-2,2-dimethylpiperidine-4-carboxylic acid (compound 20)

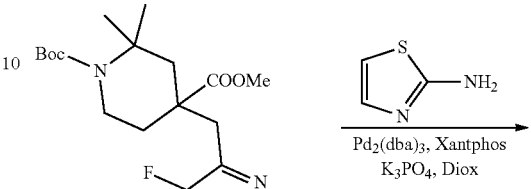

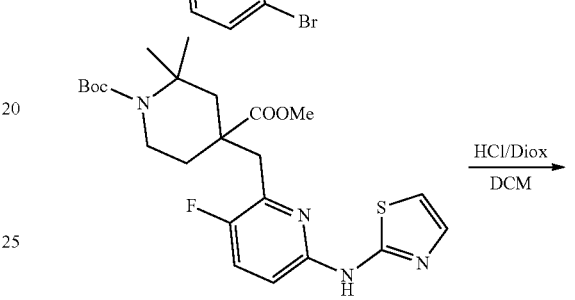

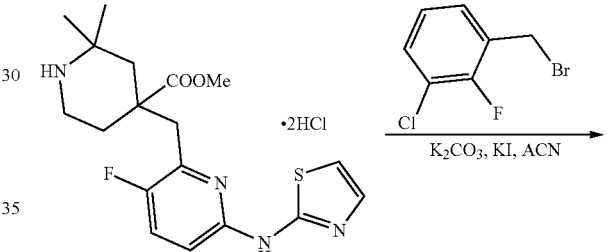

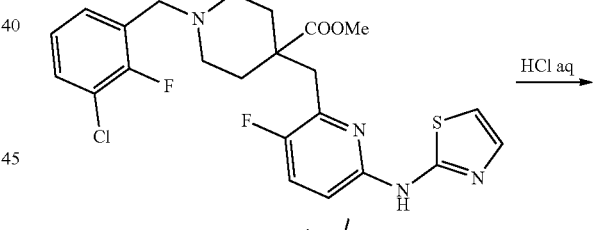

Using 1-(tert-butyl) 4-methyl 4-((6-bromo-3-fluoropyridin-2-yl)methyl)-2,2-dimethylpiperidine-1,4-dicarboxylate and thiazol-2-amine as starting materials, the target compound was obtained by the same synthetic method in example 1.

¹H NMR (400 MHz, CD₃OD) δ: 7.76 (t, J=8.7 Hz, 1H), 7.70-7.51 (m, 3H), 7.35-7.24 (m, 2H), 7.18 (dd, J=8.8, 2.9 Hz, 1H), 4.61 (d, J=13.3 Hz, 1H), 4.32 (dd, J=13.6, 8.3 Hz,

1H), 3.94 (s, 2H), 3.34-3.22 (m, 2H), 2.31 (s, 2H), 2.02-1.81 (m, 2H), 1.45 (s, 6H); ESI-MS m/z: 508.2 [M+H]⁺.

Example 21 Synthesis of 1-((3-chloro-2-fluorophenyl)methyl-d₂)-4-((3-fluoro-6-(thiazol-2-ylamino)pyridin-2-yl)methyl)-2,2-dimethylpiperidine-4-carboxylic acid (compound 21)

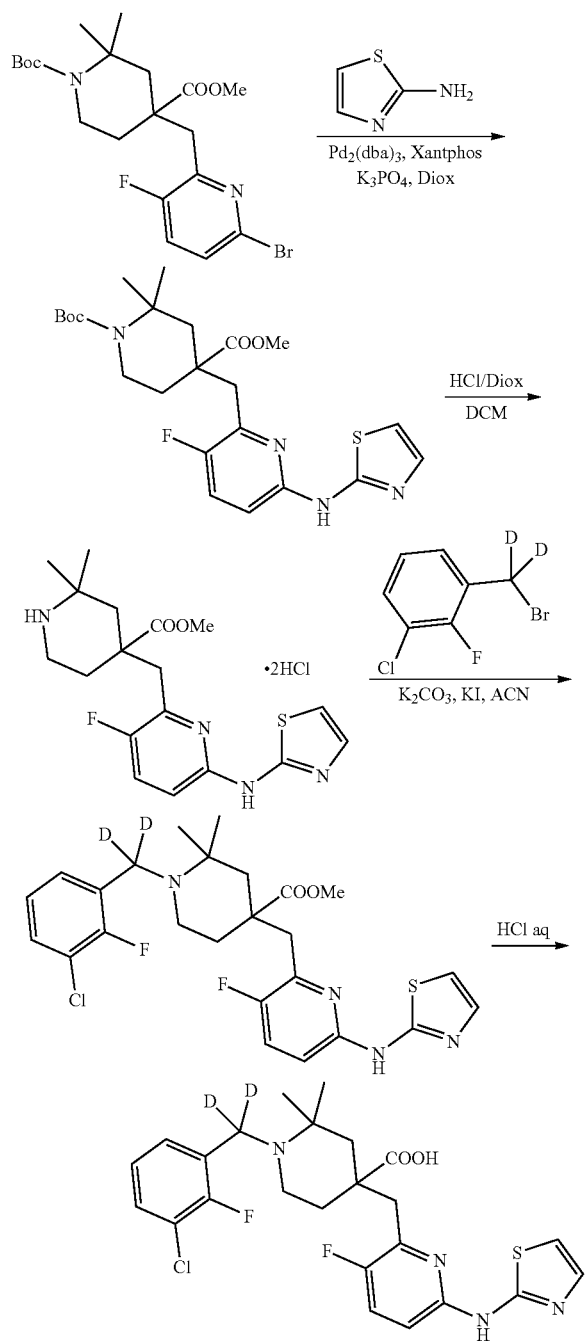

Using 1-(tert-butyl) 4-methyl 4-((6-bromo-3-fluoropyridin-2-yl)methyl)-2,2-dimethylpiperidine-1,4-dicarboxylate and thiazol-2-amine as starting materials, the target compound was obtained by the same synthetic method in example 1.

$^1$H NMR (400 MHz, CD₃OD) δ: 7.75 (t, J=8.7 Hz, 1H), 7.70-7.55 (m, 3H), 7.37-7.26 (m, 2H), 7.20 (dd, J=8.8, 2.9 Hz, 1H), 3.96 (s, 2H), 3.57-3.44 (m, 2H), 2.32 (s, 2H), 2.02-1.85 (m, 2H), 1.43 (s, 6H); ESI-MS m/z: 509.2 [M+H]⁺.

Example 22 Synthesis of 1-(3-chloro-2-fluorobenzoyl)-4-((3-fluoro-6-((5-methyl-1H-pyrazol-3-yl)amino)pyridin-2-yl)methyl)-2-methylpiperidine-4-carboxylic acid (example 22)

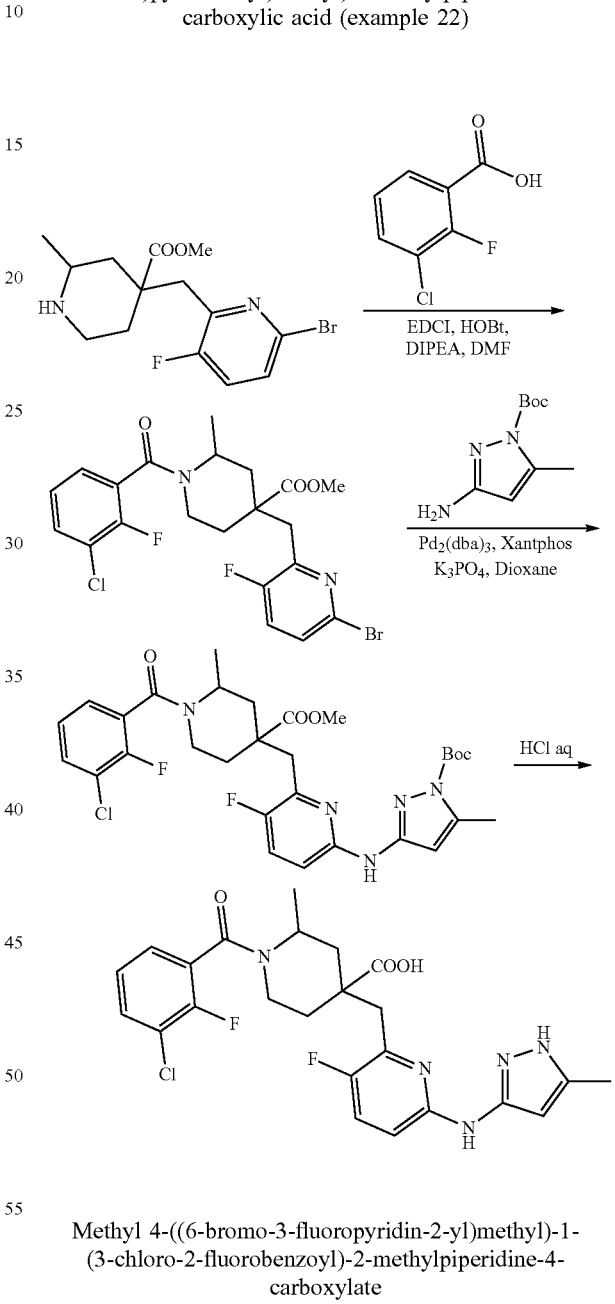

Methyl 4-((6-bromo-3-fluoropyridin-2-yl)methyl)-1-(3-chloro-2-fluorobenzoyl)-2-methylpiperidine-4-carboxylate 3-Chloro-2-fluorobenzoic acid (262 mg, 1.50 mmol), DMF (20 mL), EDCI (431 mg, 2.25 mmol), HOBt (304 mg, 2.25 mmol) and DIPEA (970 mg, 7.52 mmol) was added to a 100 mL flask, the mixture was stirred at room temperature for 30 min under the protection of Ar, methyl 4-((3-fluoro-6-(thiazol-2-ylamino)pyridin-2-yl)methyl)-2-methylpiperidine-4-carboxylate (345 mg, 1.0 mmol) was added, then stirred at room temperature for 20 h, After the completion of the reaction by LC-MS monitoring, quench with water (40 mL), exacted with EA (50 mL*2), combined with the organic phase and washed with saturated NaCl solution, concentrated, the residual was purified by column chromatography to obtain the desired intermediate (426 mg, yield 85%), ESI-MS m/z: 501.1/503.1 [M+H]+.

1-(3-Chloro-2-fluorobenzoyl)-4-((3-fluoro-6-((5-methyl-1H-pyrazol-3-yl)amino)pyridin-2-yl)methyl)-2-methylpiperidine-4-carboxylic acid Methyl 4-((6-bromo-3-fluoropyridin-2-yl)methyl)-1-(3-chloro-2-fluorobenzoyl)-2-methylpiperidine-4-carboxylate (426 mg, 0.85 mmol), tert-butyl 3-amino-5-methyl-1H-pyrazole-1-carboxylate (201 mg, 1.02 mmol), $Pd_2(dba)_3$ (92 mg, 0.10 mmol), Xantphos (116 mg, 0.20 mmol), $K_3PO_4$ (96 mg, 0.45 mmol) and 1,4-dioxane (10 mL) were added to a 100 mL flask, heated to 100° C. and further reacted for about 5 h under the protection of Ar. After the completion of the reaction determined by LC-MS, it was concentrated under reduced pressure, and further purified by column chromatography (DCM/MeOH=10/0 to 5/1) to offer the desired product as a yellow foam (394 mg, yield 75%), ESI-MS m/z: 618.1 [M+H]+.

Using abovementioned intermediate as starting materials, the target compound was obtained by the same synthetic method in example 1.

$^1$H NMR (400 MHz, $CD_3OD$) δ: 7.65 (dt, J=16.0, 8.4 Hz, 3H), 7.35 (t, J=7.9 Hz, 1H), 6.92 (dd, J=9.0, 3.1 Hz, 1H), 6.14-6.05 (m, 1H), 3.93 (dd, J=11.5, 6.1 Hz, 1H), 2.57-2.49 (m, 3H), 2.40 (s, 3H), 2.23-2.00 (m, 4H), 1.61-1.48 (m, 3H); ESI-MS m/z: 504.2 [M+H]+.

Example 23 Synthesis of 1-((3-chloro-2-fluorophenyl)methyl-$d_2$)-4-((3-fluoro-6-((5-methyl-1H-pyrazol-3-yl)amino)pyridin-2-yl)methyl)-2-methylpiperidine-4-carboxylic acid (example 23)

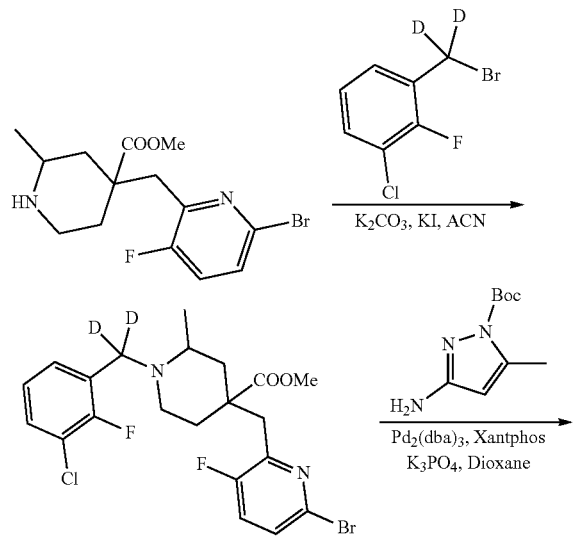

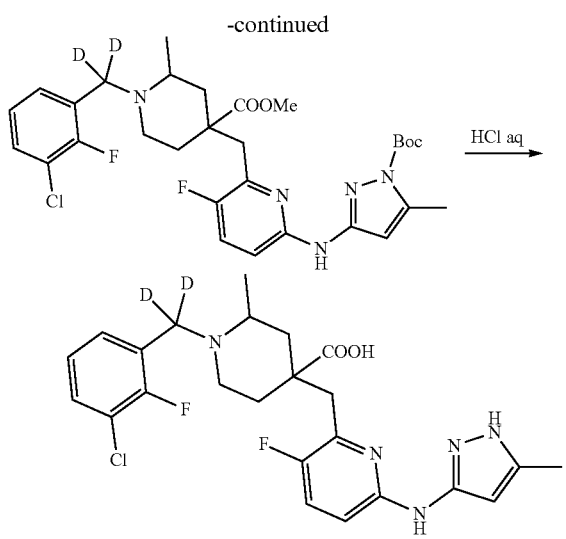

Methyl 4-((6-bromo-3-fluoropyridin-2-yl)methyl)-1-((3-chloro-2-fluorophenyl)methyl-$d_2$)-2-methylpiperidine-4-carboxylate 1-(tert-Butyl) 4-methyl 4-((6-bromo-3-fluoropyridin-2-yl)methyl)-2-methylpiperidine-1,4-dicarboxylate (1 g, 2.62 mmol, it was synthesized by referring to the method in patent WO2016077161), 1-(bromomethyl-$d_2$)-3-chloro-2-fluorobenzene (650 mg, 2.88 mmol), $K_2CO_3$ (1.811 g, 13.1 mmol), KI (10 mg) and ACN (20 mL) were added to a 100 mL flask, stirred at room temperature for about 2 h. After the completion of the reaction determined by LC-MS, concentrated and further purified by column chromatography (PE/EA=20/1 to 8/1) to offer methyl 4-((6-bromo-3-fluoropyridin-2-yl)methyl)-1-((3-chloro-2-fluorophenyl)-methyl-d2)-2-methylpiperidine-4-carboxylate (985 mg, yield 77%) as colorless oil, ESI-MS m/z: 489.1/491.1 [M+H]+.

Methyl 4-((6-((1-(tert-butoxycarbonyl)-5-methyl-1H-pyrazol-3-yl)amino)-3-fluoropyri-din-2-yl)methyl)-1-((3-chloro-2-fluorophenyl)methyl-$d_2$)-2-methylpiperidine-4-carboxylate Methyl 4-((6-bromo-3-fluoropyridin-2-yl)methyl)-1-((3-chloro-2-fluorophenyl)-methyl-d2)-2-methylpiperidine-4-carboxylate (985 mg, 2.01 mmol), tert-butyl 3-amino-5-methyl-1H-pyrazole-1-carboxylate (476 mg, 2.41 mmol), $Pd_2(dba)_3$ (92 mg, 0.10 mmol), Xantphos (116 mg, 0.20 mmol), $K_3PO_4$ (1.067 mmol) and 1,4-dioxane (20 mL) were added to a 100 mL flask, heated to 100° C. and further reacted for 5 h under the protection of Ar. After the completion of the reaction determined by LC-MS, it was concentrated and further purified by column chromatography (PE/EA=10/1 to 5/1) to offer the desired intermediate as yellow forma (1.03 g, yield 84%), ESI-MS m/z: 605.3 [M+H]+.

1-((3-Chloro-2-fluorophenyl)methyl-$d_2$)-4-((3-fluoro-6-((5-methyl-1H-pyrazol-3-yl)amino)pyridin-2-yl)methyl)-2-methylpiperidine-4-carboxylic acid Methyl 4-((6-((1-(tert-butoxycarbonyl)-5-methyl-1H-pyrazol-3-yl)amino)-3-fluoropyridin-2-yl)methyl)-1-((3-chloro-2-fluorophenyl)methyl-$d_2$)-2-methylpiperidine-4-carboxylate (1.03 g, 1.70 mmol) was added to a 100 mL flask, then water (15 mL) and con. HCl (15 mL) were added, heated to 105° C. and refluxed for 5 h. After the completion of the reaction determined by LC-MS, it was concentrated and the residual was slurred with ACN (30 mL) at room temperature. After filtration, the filter cake was washed with ACN (5 mL*2), and dried to obtain the desired yellow powder (844 mg, yield 88%).

$^1$H NMR (400 MHz, CD$_3$OD) δ: 7.63 (dt, J=16.0, 8.4 Hz, 3H), 7.32 (t, J=7.9 Hz, 1H), 6.90 (dd, J=9.0, 3.1 Hz, 1H), 6.04-6.01 (m, 1H), 3.96 (dd, J=11.5, 6.1 Hz, 1H), 3.58-3.30 (m, 4H), 2.40 (s, 3H), 2.23-2.00 (m, 5H), 1.61-1.48 (m, 3H); ESI-MS m/z: 492.2 [M+H]$^+$.

Example 24 Synthesis of 1-(3-chloro-2-fluorobenzyl)-4-((6-((5-cyclopropyl-1H-pyrazol-3-yl)amino)-3-fluoropyridin-2-yl)methyl)-2-methylpiperidine-4-carboxylic acid (compound 24)

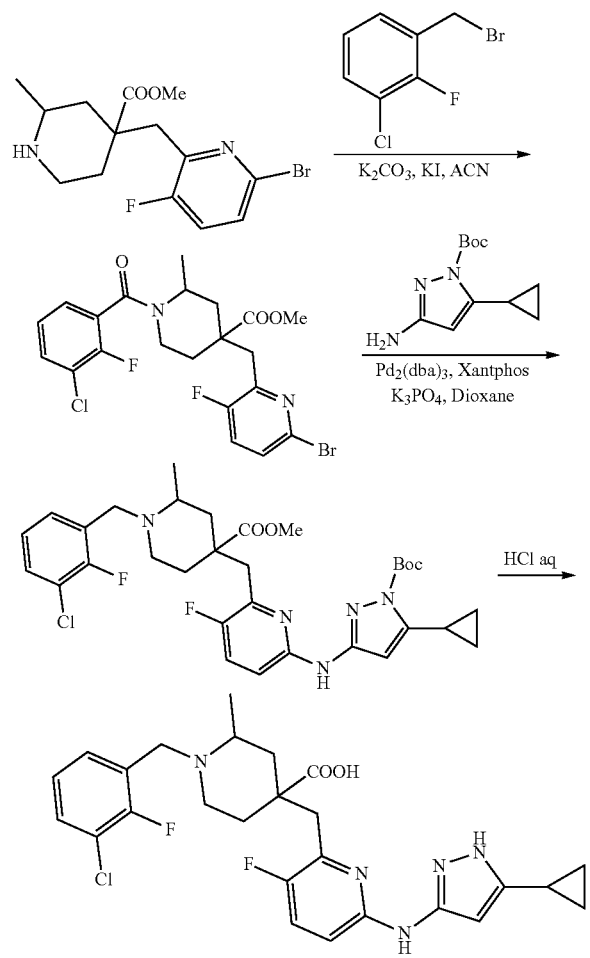

Using methyl 4-((6-bromo-3-fluoropyridin-2-yl)methyl)-2-methylpiperidine-4-carboxylate and 1-(bromomethyl)-3-chloro-2-fluorobenzene as starting materials, the target compound was obtained by the same synthetic method in example 23.

$^1$H NMR (400 MHz, CD$_3$OD) δ: 7.61 (dt, J=16.0, 8.4 Hz, 3H), 7.34 (t, J=7.9 Hz, 1H), 6.85 (dd, J=9.0, 3.1 Hz, 1H), 6.01-5.95 (m, 1H), 4.56 (d, J=13.3 Hz, 1H), 4.13 (dd, J=13.6, 8.3 Hz, 1H), 3.93 (dd, J=11.5, 6.1 Hz, 1H), 3.68-3.41 (m, 4H), 2.23-2.00 (m, 4H), 1.61-1.48 (m, 4H), 0.85-0.67 (m, 4H); ESI-MS m/z: 516.2 [M+H]$^+$.

Example 25 Aurora Kinase Activity Assay

The Caliper mobility shift assay was used to measure compound activity towards aurora kinase. 10 different concentrations of compounds were prepared by three-fold serial dilutions. Recombinant Aurora kinases in kinase buffer (20 mM HEPES, pH 7.5, 0.01% Triton X-100) were incubated with compounds for 10 minutes at room temperature. FAM labeled peptide substrates were subsequently added to initiate the reaction at 25° C. Conversion rates were measured by caliper after the reactions were terminated. LY-3295668 was used as positive control. Data were normalized to that of the vehicle control, and percentage of inhibition and IC$_{50}$ were calculated. Results were listed in Table 2.

Example 26 H1975 Proliferation Assay

H1975 cells growing in logarithmic phase were trypsinized, triturated into single cell suspensions and seeded in 384 plates at a density of 5×10$^3$/well in 50 mL. Cells were allowed to attach overnight and compounds were added to the cells for a further incubation of 72 hours. 50 mL of CTL was added afterwards to measure cell survival through ATP quantification. IC$_{50}$ was calculated with GRAPHPAD and listed in Table 2.

TABLE 2

| | IC$_{50}$ Values for Aurora kinase Inhibition and anti-Proliferation of H1975 | | |
|---|---|---|---|
| | Aurora IC$_{50}$ (nM) | | H1975 |
| Compound | A | B | IC$_{50}$ (μM) |
| 1 | 0.64 | 20 | 0.022 |
| 1-1 | 0.4 | 16 | 0.012 |
| 3 | 0.73 | 321 | 0.195 |
| 7 | 1.10 | 822 | 0.099 |
| 9 | 0.98 | 126 | 0.081 |
| 13 | 0.74 | 15 | 0.025 |
| 20 | 1.42 | 435 | 0.156 |
| 22 | 1.21 | 1142 | 0.155 |
| 23 | 0.66 | 1955 | 0.415 |
| LY-3295668 | 0.86 | 1440 | 0.102 |

As listed above, compounds of general formula (1), wherein L is of proper size such as CD$_2$ instead of CH$_2$ and/or W is

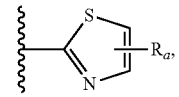

show improved potency towards Aurora-A, Aurora-B and H1975. Optical isomers in this disclosure exhibit differential activities from the racemic mixtures. For example, the optical isomer, compound 1-1, is more potent than its racemic mixture, compound 1. The activities of other optical isomers of the present disclosure can be similarly measured and may exceed that of compound 1-1.

Example 27 In Vivo Anti-Tumor Growth in H1975 Mouse Xenografts

H1975 cells were cultured in 1640 medium containing 10% FBS at 37° C. and with 5% CO$_2$. Cells were passaged and harvested by trypsinization. 8×10⁶ cells were implanted in the left armpit of nude mice. Mice were randomized into four groups of 6 mice each when the tumor volume reaches about 80 mm³, and were dosed with vehicle, and 6 mg/ml LY-3295668, compound 13 and compound 23 at 0.1 mg/10 g respectively by oral gavage. Tumor volume and body weight were monitored every other day. Mice were sacrificed on day 21 of treatment. Relative tumor volume (RTV) and tumor growth (T/C), and tumor growth inhibition (TGI) were calculated and analyzed. The result is listed in Table 3.

display markedly improved efficacy in vivo, which is of great significance for targeting cancer with aurora kinase inhibitors.

Example 28 In Vivo Anti-Tumor Growth in H69 Mouse Xenografts

H69 cells were cultured in 1640 medium containing 10% FBS at 37° C. and with 5% $CO_2$. Cells were passaged and harvested by trypsinization. 1×10⁷ H69 cells were implanted

TABLE 3 in vivo efficacy in mouse H1975 xenograft models

| Compound | Dosage | Schedule | Body weight (g) D1 | Body weight (g) D21 | Tumor volume (mm³) D1 | Tumor volume (mm³) D21 | RTV | T/C | TGI (%) |
|---|---|---|---|---|---|---|---|---|---|
| Vehicle control | (—) | qd*21 | 17.63 ± 0.52 | 19.37 ± 0.59 | 82.94 ± 6.96 | 1621.28 ± 215.82 | 19.57 ± 2.67 | (—) | (—) |
| LY-3295668 | 60 | qd*21 | 17.85 ± 0.45 | 18.58 ± 0.46 | 82.56 ± 7.60 | 611.95 ± 80.83** | 7.66 ± 1.16** | 39.17 | 65.59 |
| 13 | 60 | qd*21 | 17.82 ± 0.45 | 19.00 ± 0.68 | 82.50 ± 7.11 | 373.74 ± 35.20*** | 4.72 ± 0.59*** | 24.11 | 81.07 |
| 23 | 60 | qd*21 | 18.10 ± 0.22 | 18.47 ± 0.21 | 82.75 ± 6.63 | 590.77 ± 86.75** | 6.98 ± 0.58*** | 35.65 | 66.98 |

*P < 0.05 vs control,
**P < 0.01 vs control,
***P < 0.001 vs control,
****: P < 0.0001 vs control;
D1: first day of treatment;
D21: the last day of treatment;
qd*21: once per day for 21 days:
RTV: Relative tumor volume:
RTV = $V_t/V_0$;
T/C (%) = $T_{RTV}/C_{RTV}$ × 100;
$T_{RTV}$: relative tumor volume (RTV) of the treatment group;
$C_{RTV}$: relative tumor volume (RTV) of the vehicle control group.
TGI: tumor growth inhibition (%);
T/C (%) > 60%: ineffective;
T/C (%) ≤ 60% and P < 0.05: effective.

As listed in Table 3, compared with LY-3295668, compound 13 shows greater activity in vivo, suggesting that compounds of general formula (1), wherein Lis of proper size such as $CD_2$, and/or W is

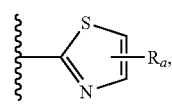

in the left armpit of nude mouse. Mice were randomly allocated to four groups of 8 mice each when the tumor volume reaches about 290 mm³, and were orally given vehicle (0.5% MC), and 2.5 mg/kg, 5 mg/kg and 10 mg/kg compound 1-1 twice daily respectively. Tumor volume and body weight were measured every other day. Mice were sacrificed on day 21 of treatment. Relative tumor volume (RTV) and tumor growth (T/C), and tumor growth inhibition (TGI) were calculated and analyzed statistically. Results are listed below.

TABLE 4 in vivo efficacy in mouse H69 xenograft models

| Compound | Dosage (mg/kg) | Schedule | Body weight (g) D1 | Body weight (g) D21 | Tumor volume (mm³) D1 | Tumor volume (mm³) D21 | RTV | T/C | TGI (%) |
|---|---|---|---|---|---|---|---|---|---|
| Vehicle | (—) | bid*21 | 15.56 ± 0.16 | 17.57 ± 0.26 | 292.98 ± 17.27 | 1250.29 ± 81.43 | 3.30 ± 0.7 | (—) | (—) |
| LY-3295668 | 10 | bid*21 | 16.70 ± 0.41 | 17.03 ± 0.36 | 289.65 ± 17.05 | 516.75 ± 108.38 | 1.74 ± 0.94**** | 0.53 | 76.28 |
| 1-1 | 2.5 | bid*21 | 15.99 ± 0.27 | 16.73 ± 0.40 | 287.46 ± 16.23 | 180.58 ± 30.15 | 0.65 ± 0.38**** | 0.20 | 111.16 |
| 1-1 | 5 | bid*21 | 15.91 ± 0.25 | 16.01 ± 0.38 | 284.84 ± 20.53 | 90.43 ± 13.11 | 0.33 ± 0.17**** | 0.10 | 120.31 |

TABLE 4-continued in vivo efficacy in mouse H69 xenograft models

| Compound | Dosage (mg/kg) | Schedule | Body weight (g) D1 | D21 | Tumor volume (mm³) D1 | D21 | RTV | T/C | TGI (%) |
|---|---|---|---|---|---|---|---|---|---|
| 1-1 | 10 | bid*21 | 16.16 ± 0.41 | 16.19 ± 0.55 | 287.92 ± 21.01 | 93.16 ± 18.83 | 0.37 ± 0.16**** | 0.11 | 120.34 |

*P < 0.05 vs control,
**: P < 0.01 vs control,
***: P < 0.001 vs control,
****P < 0.0001 vs control;
D1: first day of treatment;
D21: the last day of treatment;
qd*21: once per day for 21 days;
RTV: Relative tumor volume:
RTV = $V_t/V_0$;
T/C (%) = $T_{RTV}/C_{RTV}$ × 100;
$T_{RTV}$: relative tumor volume (RTV) of the treatment group;
$C_{RTV}$: relative tumor volume (RTV) of the vehicle control group;
TGI: tumor growth inhibition (%);
T/C (%) > 60%; ineffective;
T/C (%) ≤ 60% and P < 0.05: effective.

As presented in Table 4, compound 1-1 blocks H69 tumor growth in a dose dependent manner with markedly improved efficacy compared to LY-3295668.

While specific embodiments of the invention have been described above, it will be understood by those skilled in the art that these are merely examples, and various changes or modifications may be made to these embodiments without departing from the principles and spirit of the invention. Accordingly, the scope of the invention is defined by the appended claims.

The invention claimed is:

1. A compound of formula (1), an optical isomer, a crystalline form, or a pharmaceutically acceptable salt thereof:

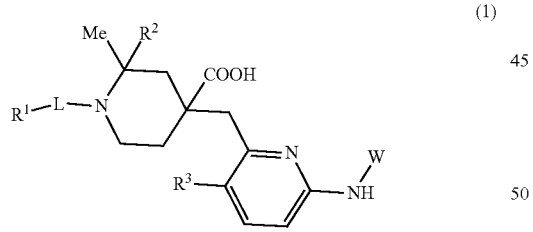

in formula (1):
$R^1$ is aryl, heteroaryl,

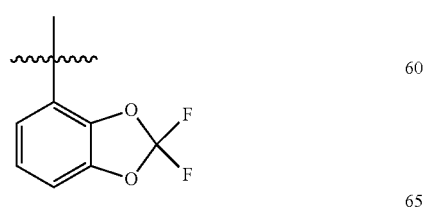

or

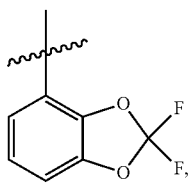 [SMILES: *c1cccc2c1OC(F)(F)O2]

wherein the aryl and the heteroaryl is optionally substituted by 1-3 groups selecting from the group consisting of halogen, C1-C3 alkyl, C1-C3 alkoxyl, halogen substituted C1-C3 alkyl and halogen substituted C1-C3 alkoxyl;
$R^2$ is H or methyl;
$R^3$ is H or F;
W is

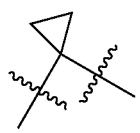

wherein $R_a$ is H, C1-C3 alkyl or C3-C6 cycloalkyl; and
L is $CH_2$, CO, $CD_2$, CH(Me), $C(Me)_2$,

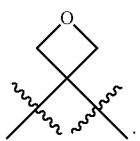 [SMILES: *C1(*)COC1]

.

2. The compound according to claim 1, wherein in formula (1), $R^1$ is

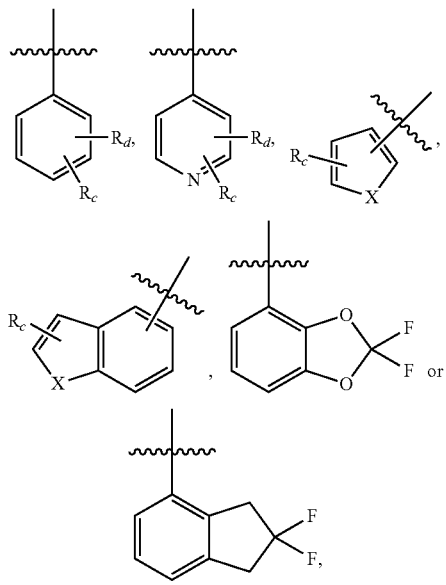

wherein X is NH, O or S, $R_c$ and $R_d$ are independently H, halogen, C1-C3 alkyl, C1-C3 alkoxyl, halogen substituted C1-C3 alkyl or halogen substituted C1-C3 alkoxyl.

3. The compound according to claim 2, wherein in formula (1), $R^1$ is

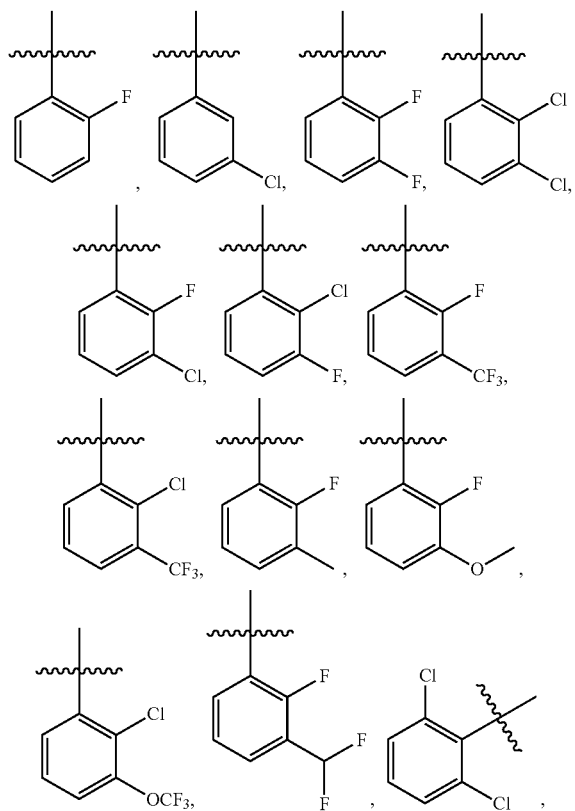

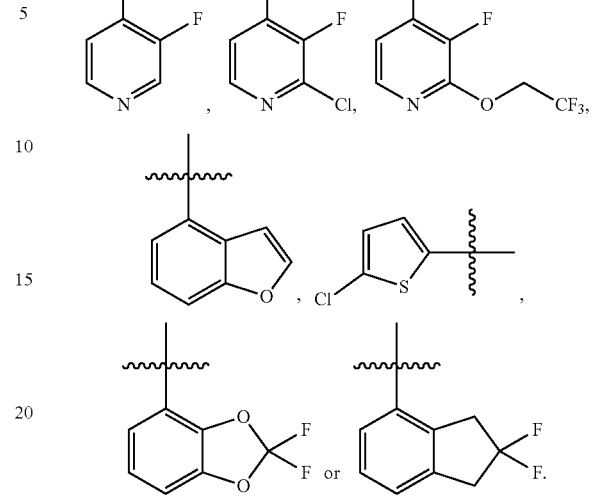

4. The compound according to claim 1, or a pharmaceutically acceptable salt thereof, wherein the compound is:

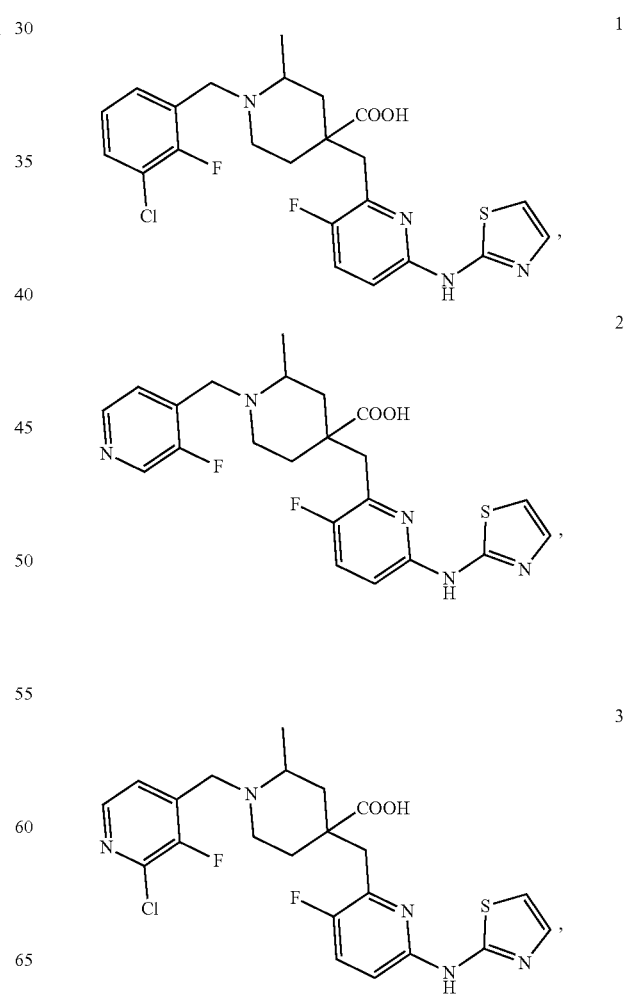

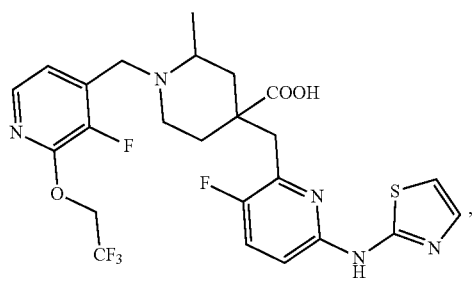
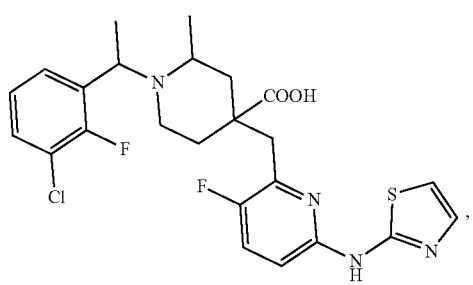
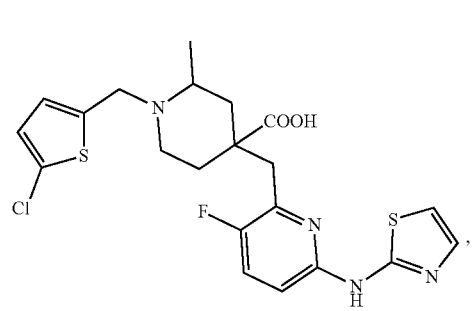
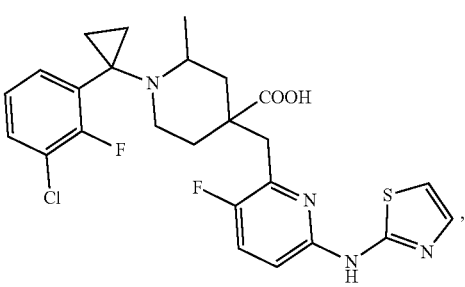
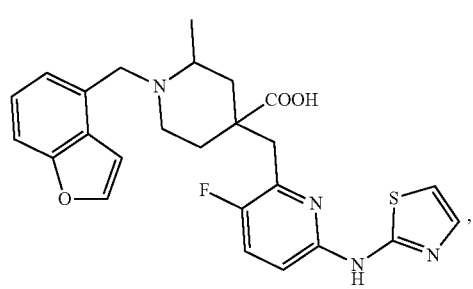
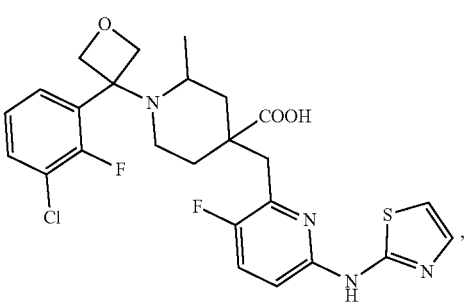
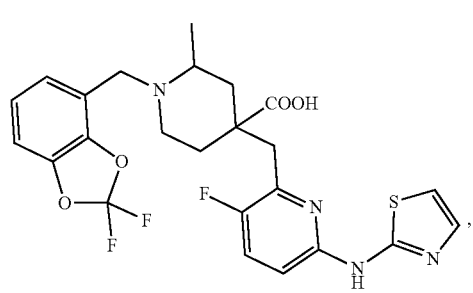
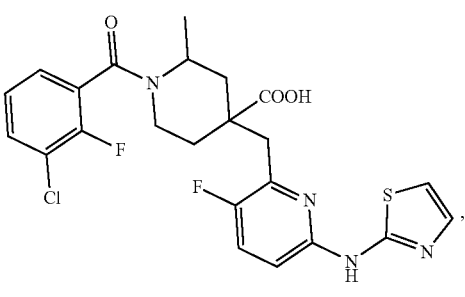
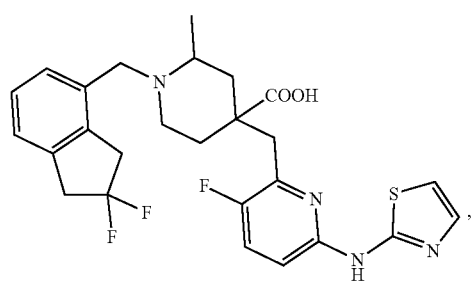
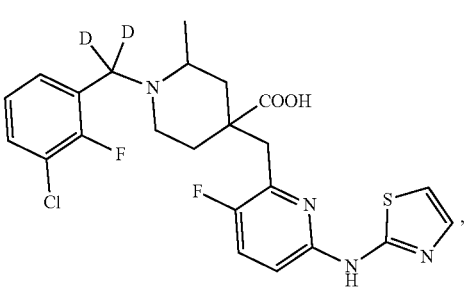

14
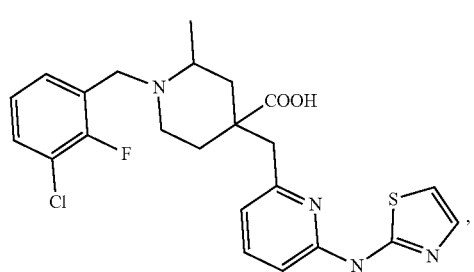
,
15
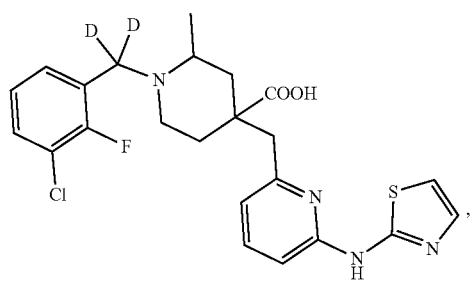
,
16
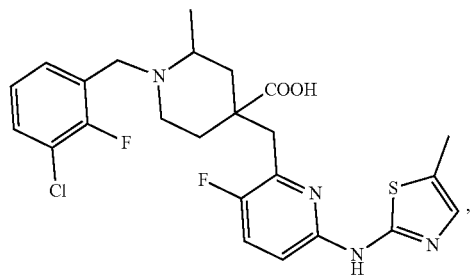
,
17
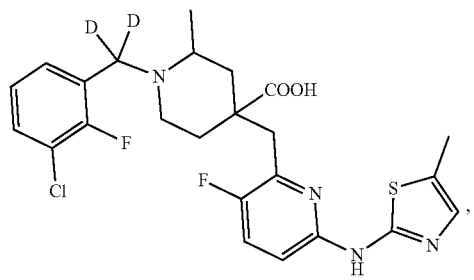
,
18
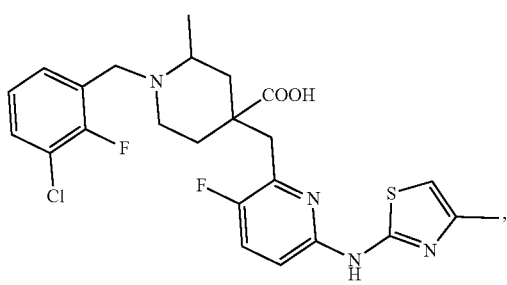
,
19
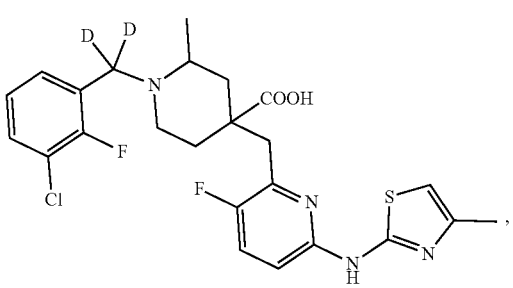
,
20
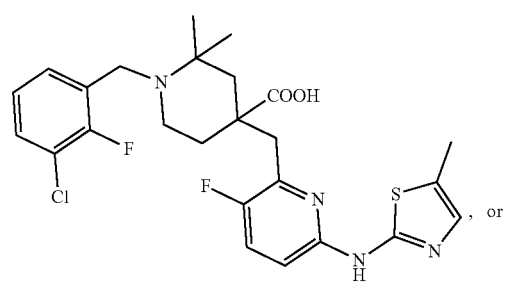
, or
21
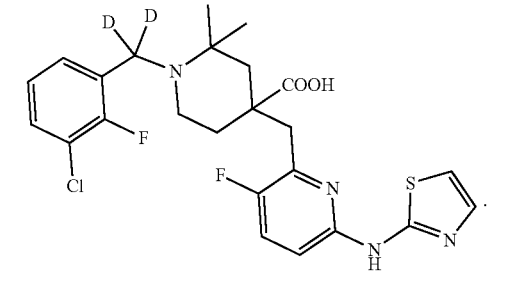
.
5. An aurora kinase inhibitor composition comprising the compound according to claim 1, an optical isomer, a crystalline form or a pharmaceutically acceptable salt as an active ingredient.
6. A combination pharmaceutical composition, comprising the compound according to claim 1 as an active ingredient and a pharmaceutically acceptable carrier or diluent.
* * * * *